United States Patent [19]
Byers et al.

[11] Patent Number: 4,766,550
[45] Date of Patent: Aug. 23, 1988

[54] AUTOMATIC ON-LINE CHEMISTRY MONITORING SYSTEM

[75] Inventors: William A. Byers, Penn Hills Twp., Allegheny County; Gerald L. Carlson, Mt. Lebanon; David F. Pensenstadler, North Huntingdon; Michael J. Wootten, Murrysville; James E. Richards, Monroeville, all of Pa.

[73] Assignee: Westinghouse Electric Corp., Pittsburgh, Pa.

[21] Appl. No.: 793,061

[22] Filed: Oct. 30, 1985

[51] Int. Cl.$^4$ .................. G06F 15/46; G01N 31/00; G01L 3/26
[52] U.S. Cl. .................. 364/497; 422/62; 73/112; 73/863.01; 73/861.33; 364/556; 364/571
[58] Field of Search ............ 73/112, 863.01, 863.31, 73/863.33, 864.81; 364/497, 499, 500, 496, 556, 571; 422/62

[56] References Cited

U.S. PATENT DOCUMENTS

| | | | |
|---|---|---|---|
| 3,826,905 | 7/1974 | Valkama et al. | 364/498 |
| 3,972,804 | 8/1976 | McLaughlin et al. | 364/500 |
| 4,064,392 | 12/1977 | Desalu | 364/492 |
| 4,181,951 | 1/1980 | Boeke | 364/499 |
| 4,206,504 | 6/1980 | Frey | 364/497 |
| 4,218,746 | 8/1980 | Koshiiski | 364/497 |
| 4,251,503 | 2/1981 | Swindells et al. | 364/497 |
| 4,298,955 | 11/1981 | Munday et al. | 364/900 |
| 4,308,463 | 12/1981 | Geras et al. | 364/494 |
| 4,326,940 | 4/1982 | Eckles et al. | 364/500 |
| 4,384,925 | 5/1983 | Stetter et al. | 364/497 |
| 4,390,348 | 6/1983 | Dille et al. | 364/500 |
| 4,414,858 | 11/1983 | Peterson et al. | 73/863.33 |
| 4,424,559 | 1/1984 | Lorinez et al. | 364/131 |
| 4,460,967 | 7/1984 | Krull et al. | 364/497 |
| 4,472,354 | 9/1984 | Passell et al. | 422/63 |
| 4,597,299 | 7/1986 | Campbell et al. | 73/864.81 |
| 4,631,687 | 12/1986 | Kowalski et al. | 364/497 |
| 4,641,249 | 2/1987 | Gion et al. | 364/496 |
| 4,644,479 | 2/1987 | Kemper et al. | 364/550 |
| 4,663,724 | 5/1987 | Onizuka et al. | 364/497 X |

Primary Examiner—Parshotam S. Lall
Assistant Examiner—Joseph L. Dixon

[57] ABSTRACT

A system for automatically sampling, monitoring and analyzing power plant steam cycle water supplied from various points in a power plant steam cycle system as a plurality of influent fluid sample streams. A continuous monitor module including continuous on-line monitors and a calibration unit provides continuous on-line monitoring of each influent fluid sample stream, and an ion chromatograph unit provides semi-continuous monitoring of a selected one of the influent fluid sample streams. Each calibration unit is operable to condition the corresponding influent fluid sample stream to provide a conditioned influent fluid sample stream having predetermined chemical characteristics; the continuous on-line monitors are calibrated with respect to the predetermined chemical characteristics of the corresponding conditioned influent fluid sample stream and the ion chromatograph unit is calibrated with respect to the predetermined chemical characteristics of the selected conditioned influent fluid sample stream supplied thereto. A control unit receives signals representative of the monitored chemical characteristics from the continuous on-line monitors and the ion chromatograph unit and uses these signals in a feedback loop to control the monitoring system and to detect, analyze and correct steam cycle water chemistry changes before corrosion or other problems related to water chemistry imbalances. The control unit controls the monitoring system by determining the sequence in which the plural influent fluid sample streams are supplied to the ion chromatograph unit, controlling the monitoring performed by the ion chromatograph unit, and automatically calibrating the continuous on-line monitors and the ion chromatograph unit.

17 Claims, 16 Drawing Sheets

AUTOMATIC ON-LINE CHEMISTRY MONITORING SYSTEM

BACKGROUND OF THE INVENTION

1. Field of the Invention

The present invention generally relates to a system for automatically sampling, monitoring and analyzing power plant steam cycle water from a plurality of points in a power plant steam system and, more particularly, to a system for performing continuous on-line chemical monitoring using continuous on-line monitors, and semi-continuous on-line monitoring using an ion chromotograph unit, for controlling the monitoring with real-time feedback from the continuous on-line monitors and the ion chromatograph unit, and for automatically analyzing the monitored chemical characteristics.

2. Description of the Related Art

The control of impurities in power plant steam cycle water is recognized as being essential to the protection of a power plant's steam system against corrosion related failures. In spite of advances in methods for detecting and measuring impurities, or contaminants, at ultra-trace concentration levels, plant chemistry monitoring is, for the most part, based on the on-line monitoring of only a few chemical characteristics, such as conductivity, pH, and dissolved oxygen concentration. Many critical impurities which cause corrosion, such as chloride and sulfate, are checked only once or twice a day by laboratory analysis of grab samples. Grab sample data, since obtained only at long intervals, provides only a historical record of plant chemistry and is of little use in controlling the levels of corrosion causing impurities and thus in the prevention of corrosion related failures. Furthermore, on-line monitor information which is available, is provided only as strip chart records which require tedious operator analysis.

In current instrumentation, particularly cation conductivity monitors, the composition of the fluid sample, or solution, to be monitored is assumed at the time that the instrument is manufactured. The calculation of temperature compensated cation conductivity values, however, is dependent on the measured cation conductivity and solution composition. Thus, temperature compensated cation conductivity values will be erroneous if the actual solution composition differs from the assumed composition. The lack of real time feedback in prior monitoring systems prevents accurate temperature compensation since the actual solution composition cannot be factored into the temperature compensation.

Current monitoring systems also suffer from a lack of integrated calibration capability. Calibration is usually a scheduled maintenance operation; thus, calibration problems or equipment failures which occur between scheduled calibrations could go undetected and uncorrected until the next scheduled calibration. Moreover, as a scheduled maintenance operation, calibration has usually been performed manually as an off-line procedure using standards which may be significantly different than the sample, for example, highly concentrated buffer solutions.

Several systems have been developed to monitor power plant steam cycle water. U.S. Pat. No. 4,414,858, Peterson et al., assigned to the Assignee of the present application, discloses a system for sampling fluids with a plurality of fluid sample lines connected to various points in a power plant steam system. A valve arrangement connects a selected fluid sample line to an analyzer, and passes the non-selected fluid samples to a common drain line which is connected back to the power plant steam system. A microprocessor controls the valve arrangement in accordance with a set of stored instructions to selectively connect each of the sample fluid lines to the analyzer in a sampling sequence, and controls the analyzer with open loop control. Each fluid sample line also includes a sensor which provides an output signal to the microprocessor, which alters the sampling sequence if a particular sensor output indicates an alarm condition. This system provides only one on-line monitor per sample stream, and thus monitors one chemical characteristic of each sample fluid stream. Further, calibration of the sensors and the analyzer is performed manually in an off-line procedure.

Another system for monitoring steam producing water is disclosed in U.S. Pat. No. 4,472,354, Passell et al. This system uses ion chromatographic analysis to provide an ion profile of the steam producing water. Plural sampling systems collect the steam producing water supplied from a multiple number of points in a power plant steam system over a five to six-hour time period, called a fill cycle. At the end of the fill cycle, the water collected in a particular sampling system is supplied to the ion chromatographs. Thus, the system does not provide for continuous on-line monitoring of the steam producing water at each point in the plant steam/water cycle, but rather a periodic monitoring of a fluid sample collected over a five to six hour period to provide an ion profile of the steam producing water flowing in the plant. This system does not employ any continuous on-line monitors, and uses open loop control of the operation of the ion chromatographs. In this system, calibration is performed by diluting a standard solution with pure water and providing the diluted solution directly to the ion chromatographs in response to an operator decision.

SUMMARY OF THE INVENTION

In accordance with the present invention, there is provided a system for automatic continuous on-line monitoring of the water chemistry of each of a plurality of influent fluid sample streams from various points in a power plant steam system. The monitoring system of the present invention combines analytical instruments and monitors with computerized control and data logging. More particularly, a continuous monitor module including continuous on-line monitors and a calibration unit provides continuous on-line monitoring of each influent fluid sample stream, and an ion chromatograph unit provides semi-continuous monitoring of species for which no simple on-line monitor is available in a selected one of the influent fluid sample streams. The system is controlled by a control unit including a microcomputer or a minicomputer. The control unit receives signals representative of the monitored chemical characteristics from the continuous on-line monitors and the ion chromatograph unit, and uses these signals in a feedback loop to detect monitor failures, to determine the sequence in which the plural influent fluid sample streams are supplied to the ion chromatograph unit, to control operation of the ion chromatograph unit, and to automatically calibrate the continuous on-line monitors and the ion chromatograph unit. The control unit also logs data from the continuous monitor modules and the ion chromatograph unit, and interfaces with a plant data center. Thus, steam cycle water chemistry changes can be detected, diagnosed, and corrected before corrosion or other problems related to water chemistry imbalances can occur.

In the monitoring system of the present invention, calibration of the continuous on-line monitors and the ion chromatograph unit is performed by conditioning the infuent fluid sample stream to produce a conditioned influent fluid sample stream having predetermined chemical characteristics. The continuous on-line monitors in each continuous monitor module are calibrated with respect to the predetermined chemical characteristics of the corresponding conditioned influent fluid sample stream and the ion chromatograph unit is calibrated with respect to the predetermined chemical characteristics of the conditioned influent fluid sample stream supplied thereto. By using a conditioned influent fluid sample stream, calibration of the monitoring system of the present invention compensates for ionic species in the sample water which affect the response of the continuous on-line monitors and the ion chromatograph unit but which do not alter the particular chemical characteristics being monitored. Conditioning of the infuent fluid sample streams is easily automated and provides for on-line calibration. Moreover, the use of a conditioned influent fluid sample stream allows the continuous on-line monitors and the ion chromatograph unit to be calibrated in the range in which monitoring is performed, rather than a range dictated by a convenient standard or a highly concentrated buffer solution.

In the monitoring system of the present invention each continuous monitor module monitors the temperature of and performs preliminary processing of the corresponding influent fluid sample stream. The preliminary processing includes, for example providing the influent fluid sample stream with a predetermined volumetric flow rate, deionizing the influent fluid sample stream, and the above-mentioned conditioning to perform calibration. Then, the continuous monitor module divides each infuent fluid sample stream into first and second influent fluid sample streams. The continuous on-line monitors, in the continuous monitor module, monitor selected chemical characteristics of the first influent fluid sample stream, and temperature and continuous monitor signals, representative of the monitored temperature and chemical characteristics, are generated. The second influent fluid sample streams provided by the continuous monitor modules are further divided into third and fourth influent fluid sample streams and a plurality of cation conductivity monitors monitor the cation conductivity of each of the third influent fluid sample streams and generate cation conductivity signals representative of the monitored cation conductivity. Each of the third and fourth influent fluid sample streams are selectively supplied to the ion chromatograph unit which performs on-line chromatographic monitoring of selected chemical characteristics, in accordance with chromatograph actuation signals, and generates chromatograph signals representative of the monitored chemical characteristics. The control unit receives the temperature, continuous monitor, cation conductivity, and chromatograph signals, determines the sampling sequence and interrupts the sampling sequence in response to an abnormal one of the output signals, stores predetermined conductivity equations and data, and performs a variety of analytical functions to control the operation of the monitoring system with a feedback loop. The functions performed by the control unit include, for example: calculating a strong acid temperature compensated cation conductivity in accordance with predetermined conductivity equations, the monitored temperature, and the chemical characteristics monitored by the ion chromatograph unit; comparing the strong acid temperature compensated cation conductivity with the monitored cation conductivity to select the chemical characteristics to be monitored by the ion chromatograph unit; generating the chromatograph actuation signals in accordance with the chemical characteristics selected by comparing the temperature compensated cation conductivity with the monitored cation conductivity; calculating a cation conductivity including organic acids at the monitored temperature; comparing the monitored temperature cation conductivity including organic acids with the monitored cation conductivity to determine if calibration is required; selectively generating the calibration actuation signals at predetermined time intervals and between the predetermined time intervals; and calibrating the continuous monitor, cation conductivity and chromatograph signals with respect to the predetermined chemical characteristics of the conditioned influent fluid sample stream.

One embodiment of a continuous monitor module comprises a continuous monitior unit including continuous on-line monitors for monitoring chemical characteristics selected from the group of sodium, dissolved oxygen, hydrazine, ammonia, pH, and specific conductivity, a deionizer unit for dionizing the deionized influent fluid sample stream, and a calibration unit for injecting a mixed standard solution into the deionized influent fluid sample stream to condition the deionized influent fluid sample stream to provide a conditioned deionized influent fluid sample stream having predetermined chemical characteristics.

One embodiment of the ion chromatograph unit comprises an anion chromatograph for monitoring anions, an organic acid chromatograph for monitoring organic acids, and a cation chromatograph for monitoring cations, each of said anion, organic acid and cation chromatographs having a sample volume control unit for preparing a sample volume of an influent fluid sample stream for monitoring in accordance with corresponding anion, organic acid, and cation chromatograph sample volume control unit actuation signals. For this embodiment of the ion chromatograph unit, the control unit calculates a sample volume of the third influent fluid sample stream to be prepared for monitoring by the anion and organic acid chromatograph sample volume control units in accordance with the monitored cation conductivity of the third influent fluid sample stream being supplied to the ion chromatograph means and generates the anion and organic acid chromatograph sample volume actuation signals based on the calculated sample volume of the third influent fluid sample stream, and calculates a sample volume of the fourth influent fluid sample stream to be prepared for monitoring by the cation chromatograph sample volume control unit in accordance with the monitored specific conductivity of the fourth influent fluid sample stream being supplied to the ion chromatograph unit and generates the cation chromatograph actuation signals based on the calculated sample volume of the fourth influent fluid sample stream.

DESCRIPTION OF THE PREFERRED EMBODIMENTS

Figure 1:
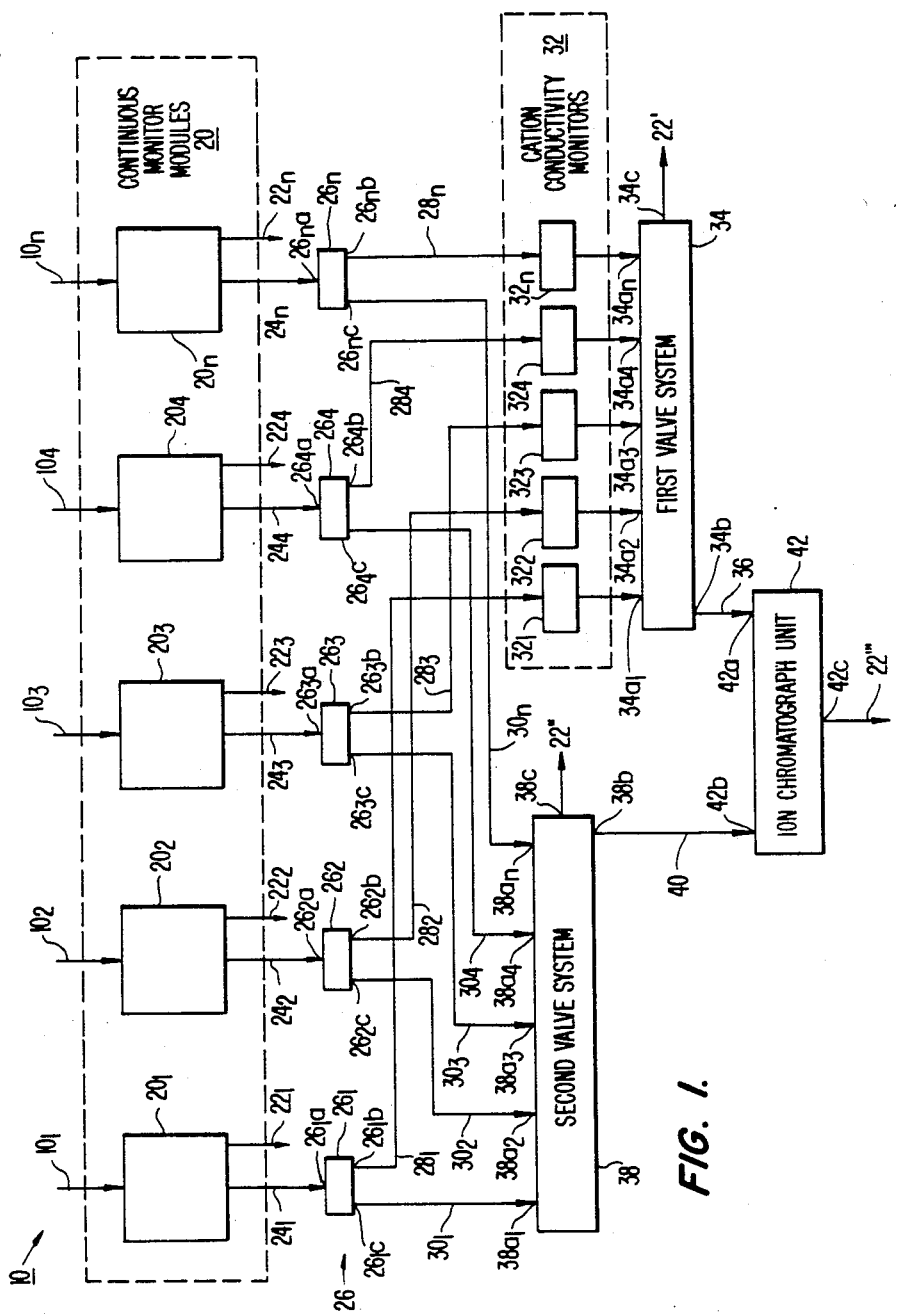
FIG. 1 is a block diagram of the monitoring system of the present invention.

The block diagram of FIG. 1 illustrates the overall monitoring system of the present invention. Fluid lines 10, individually designated $10_1$, $10_2$ ... $10_n$, supply plural influent fluid sample streams of steam cycle water from a plurality of different points in a power plant steam system to respective ones of a plurality of continuous monitor modules 20, individually designated $20_1$, $20_2$ ... $20_n$. It is to be understood that the system of the present invention may be used in any type of steam generating electrical power plant, whether fossil or nuclear fueled, and may accommodate any number of sample lines, as is deemed desirable. Each continuous monitor module 20 performs preliminary processing (described below) of the corresponding influent fluid sample stream and then divides the corresponding influent fluid sample stream received thereby into first and second influent fluid sample streams; the module 20 then analyzes the first influent fluid sample stream and thereafter directs same to a drain 22. Further, each of the modules 20 supplies a second influent fluid sample stream through a second fluid line 24 to the input 26a of a corresponding one of a plurality of second influent fluid sample stream flow-splitters 26, individually designated $26_1$, $26_2$ ... $26_n$, which divides same into third and fourth influent fluid sample streams at its outputs 26b and 26c, respectively. Corresponding ones of a plurality of third fluid lines 28 and fourth fluid lines 30 are respectively connected to the first and second outputs 26b and 26c of the second influent fluid sample stream flow-splitters 26. Cation conductivity monitors 32 are provided in each third fluid line 28 to monitor the cation conductivity of the third influent fluid sample streams and to generate cation conductivity signals representative of the monitored cation conductivities.

A first valve system 34 receives the third influent fluid sample streams from the cation conductivity monitors 32 at corresponding ones of a plurality of inputs 34a, and selectively supplies one of the third influent fluid sample streams to a first output 34b thereof and the remaining third influent fluid sample streams to the second output 34c thereof. A first valve system output line 36 is connected to the first output 34b and a drain 22' is connected to a second output 34c. A second valve system 38 receives the fourth influent fluid sample streams from the second outputs 26c of the second influent fluid sample stream flow splitters 26 at corresponding ones of a plurality of inputs 38a via the fourth fluid lines 30, and selectively supplies one of the fourth influent fluid sample streams to a first output 38b thereof and the remaining fourth influent fluid sample streams to a second output 38c thereof. A second valve system output line 40 is connected to the first output 38b and a drain 22'' is connected to the second output 38c. The first and second valve systems 34, 38 operate to supply one of each of the third and fourth influent fluid sample streams at first outputs 34b, 38b, respectively, in a sampling sequence in accordance with first and second valve system actuation signals. One example of a sampling system for use as the first and second valve systems 34, 38 is disclosed in U.S. Pat. No. 4,414,858, Peterson et al., assigned to the Assignee of the present invention, the disclosure of which is hereby incorporated by reference.

An ion chromatograph unit 42 receives the selected ones of the third and fourth influent fluid sample streams supplied by the first and second valve sytems 34, 38 at respective first and second inputs 42a, 42b through the first and second valve system output lines 36, 40. An output 42c of the ion chromatograph unit 42 is connected to a drain 22'''.

Figure 2:
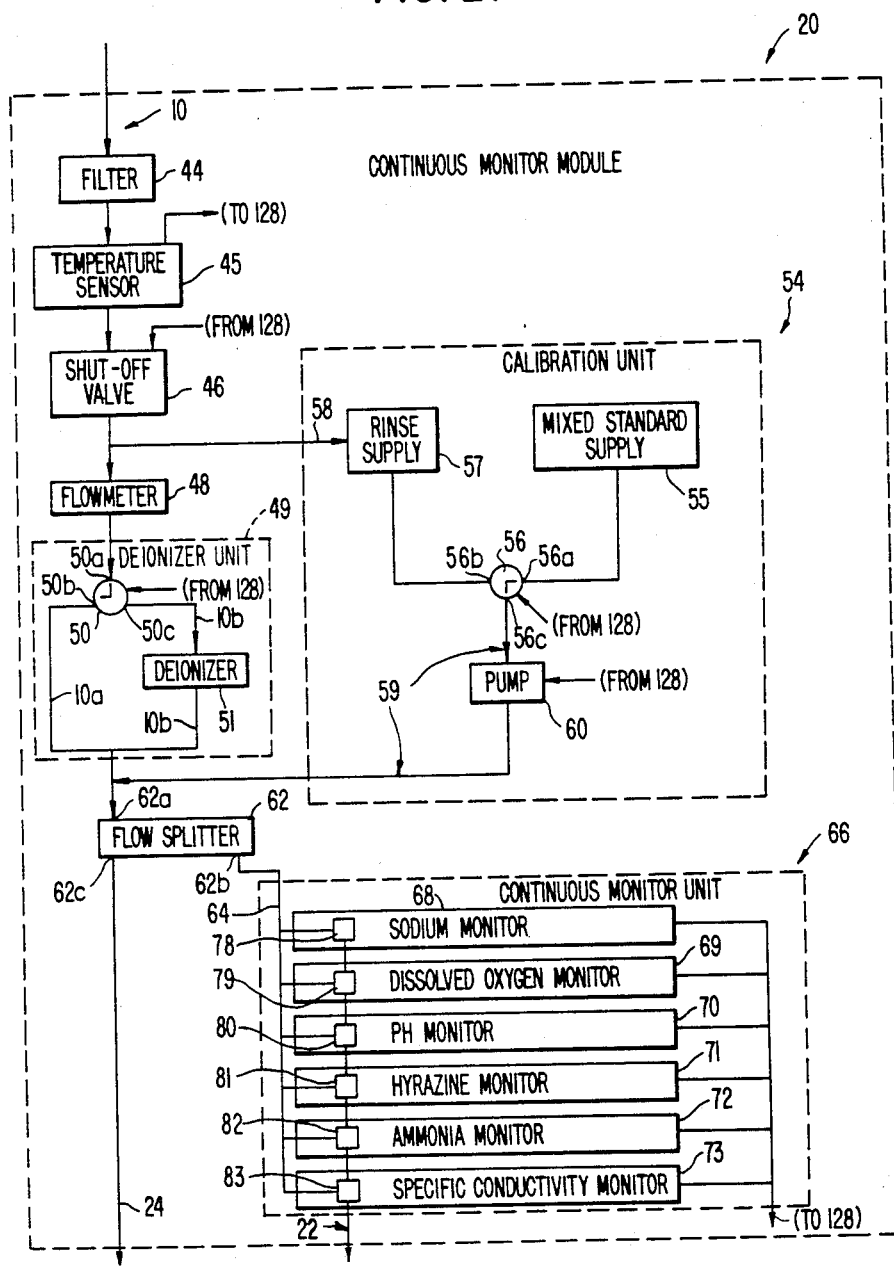
FIG. 2 is a block diagram of one embodiment of a continuous monitor module of the monitoring system.

An example of one continuous monitor module 20 is shown in the block diagram of FIG. 2. The influent fluid sample stream supplied by the fluid line 10 flows through a filter 44, a temperature sensor 45, a shut off valve 46, a flow meter 48, and a deionizer unit 49. The flowmeter 48 provides the influent fluid sample stream with a predetermined volumetric rate of flow and the temperature sensor 45 senses the temperature of the influent fulid sample stream and generates a temperature signal representative of the sensed temperature. The deionizer unit 49 includes a deionizer selector valve 50 and a deionizer 51. The deionizer selector valve 50 is selectively operable between a first position connecting its input 50a and first output 50b and a second position connecting its input 50a and second output 50c, in accordance with a deionizer selector valve actuation signal. A first parallel fluid line 10a interconnects the first output 50b of the deionizer selector valve 50 with fluid line 10 and a second parallel fluid line 10b connects the deionizer 51 to receive the influent fluid sample stream from the second output 50c of the deionizer selector valve 50 for deionizing the influent fluid sample stream and provides the deionized influent fluid sample stream to the fluid line 10.

Each continuous monitor module 20 also comprises a calibration unit 54. The calibration unit 54 includes a mixed standard supply 55 for storing a mixed standard solution having predetermined chemical characteristics, a calibration selector valve 56 having first and second inputs 56a, 56b and an output 56c, the first input 56a being in fluid communication with the mixed standard supply 55 and the second input 56b being in fluid communicaton with a rinse supply 57 for storing a rinse solution. The calibration selector valve 56 is operable between first and second positions in accordance with a calibration selector valve actuation signal, the first position connecting the first input 56a and the output 56c thereof so that the calibration selector valve 56 outputs the mixed standard solution, and the second position connecting the second input 56b and the output 56c thereof so that the calibration selector valve 56 outputs the rinse solution. A rinse supply line 58 may be provided to supply the influent fluid sample stream to the rinse supply 57. A calibration unit output line 59 connects a calibration pump 60 to receive the mixed standard solution or the rinse solution output from the output 56c of the calibration selector valve 56. The calibration pump 60 supplies the output of the valve 56 at a predetermined volumetric rate, in accordance with a calibration volume actuation signal, to inject the output of the valve 56 into the fluid line 10, and thus the influent fluid sample stream, at a point between the deionizer unit 49 and an influent fluid sample stream flow-splitter 62. The filter 44, flowmeter 48, deionizer unit 49 and calibration unit 54 perform the previously mentioned preliminary processing.

After the preliminary processing is completed the influent fluid sample stream flow-splitter 62 divides the influent fluid sample stream into first and second influent fluid sample streams at its first and second outputs 62b, 62c, respectively. A first fluid line 64 is connected to the first output 62b of the influent fluid sample stream flow-splitter 62 and the second fluid sample line 24 is connected to the second output 62c of the influent fluid sample stream flow-splitter 62.

Each continuous monitor module 20 further comprises a continuous monitor unit 66. The continuous monitor unit 66 in each continuous monitor module 20 contains as many chemical monitors as necessary to analyze the chemical characteristics of a specific infuent fluid sample stream—the chemical characteristics of each influent fluid sample stream being dependent on the particular point in the power plant steam cycle from which the influent fluid sample stream is taken. Thus, each continuous monitor unit 66 includes various continuous on-line monitors, including, for example, a sodium monitor 68, a dissolved oxygen monitor 69, a pH monitor 70, a hydrazine monitor 71 an ammonia monitor 72, and a specific conductivity monitor 73. The various monitors 68-73 comprise corresponding detectors, e.g., sodium detector 78, dissolved oxygen detector 79, pH detector 80, hydrazine detector 81, ammonia detector 82, and specific conductivity detector 83, and each detector 78-83 comprises a flow cell (not shown) and a sensor (not shown) provided in the flow cell for monitoring the level of the corresponding chemical chracteristic of a fluid sample stream. Each monitor produces an output representative of the monitored level of the corresponding chemical characteristic, the output being, for example, a visual display or an electrical signal. The continuous on-line monitors 68-73 may be standard monitors produced by Martek, Orion, Orbisphere, or Leeds & Northrup, for example.

To calibrate the monitors 68-73 in the continuous monitor unit 66, the calibration unit 54 injects a mixed standard solution from the mixed standard supply 55 into the influent fluid sample stream, to condition the influent fluid sample stream and provide a conditioned influent fluid sample stream having predetermined chemical characteristics. As previously stated, the calibration pump 60 injects the mixed standard solution at a predetermined volumetric rate in accordance with the calibration volume actuation signal, and since the influent fluid sample stream flows at a predetermined volumetric rate after passing through flow meter 48, the concentration of the mixed standard solution in the conditioned influent fluid sample stream, and thus the various chemical characteristics of the conditioned influent fluid sample stream, can be easily determined. The conditioned influent fluid sample stream is divided into conditioned first and second influent fluid sample streams by the influent fluid sample stream flow-splitter 62 and the conditioned first fluid sample stream is supplied to each of the monitors 68-73 by the first fluid line 64. The output of each of the monitors 68-73 is calibrated with respect to the predetermined chemical characteristics of the conditioned first influent fluid sample stream, as is known in the art, by a control unit which is described later. Further, the conditioned second influent fluid sample stream provided by one of the continuous monitor modules 20 can be used to calibrate the ion chromatograph unit 42. By using a conditioned influent fluid sample stream, rather than a buffer solution, to calibrate the monitors 68-73, the monitoring system of the present invention eliminates the effects on the response of the detectors 78-83 of any ionic species in the fluid sample stream which do not effect the chemical chracteristic being monitored. An on-line calibration system for chemical monitors is disclosed in a copending U.S application No. 782,858, now U.S. Pat. No. 4,713,618 assigned to the Assignee of the present invention.

In some instances it is preferable to calibrate the monitors 68-73 and the ion chromatograph unit 42 by conditioning a deionzied fluid sample stream. In this case, the deionzier selector valve 50 is actuated to connect the input 50a and the second output 50c thereof to provide the influent fluid sample stream to the deionzer 51 via the second parallel fluid sample line 10b so that the mixed standard solution is injected into a deionized influent fluid sample stream to produce a conditioned deionized influent fluid sample stream. After the montiors 68-73 in the continuous monitor unit 66 are calibrated, valve 56 is actuated to provide the rinse solution 57 or the influent fluid sample stream, supplied by the rinse supply line 58, to the calibration pump 60 to rinse the mixed standard solution from the calibration pump 60 and the calibration unit output line 59 with either the rinse solution or the influent fluid sample stream.

Figure 3:
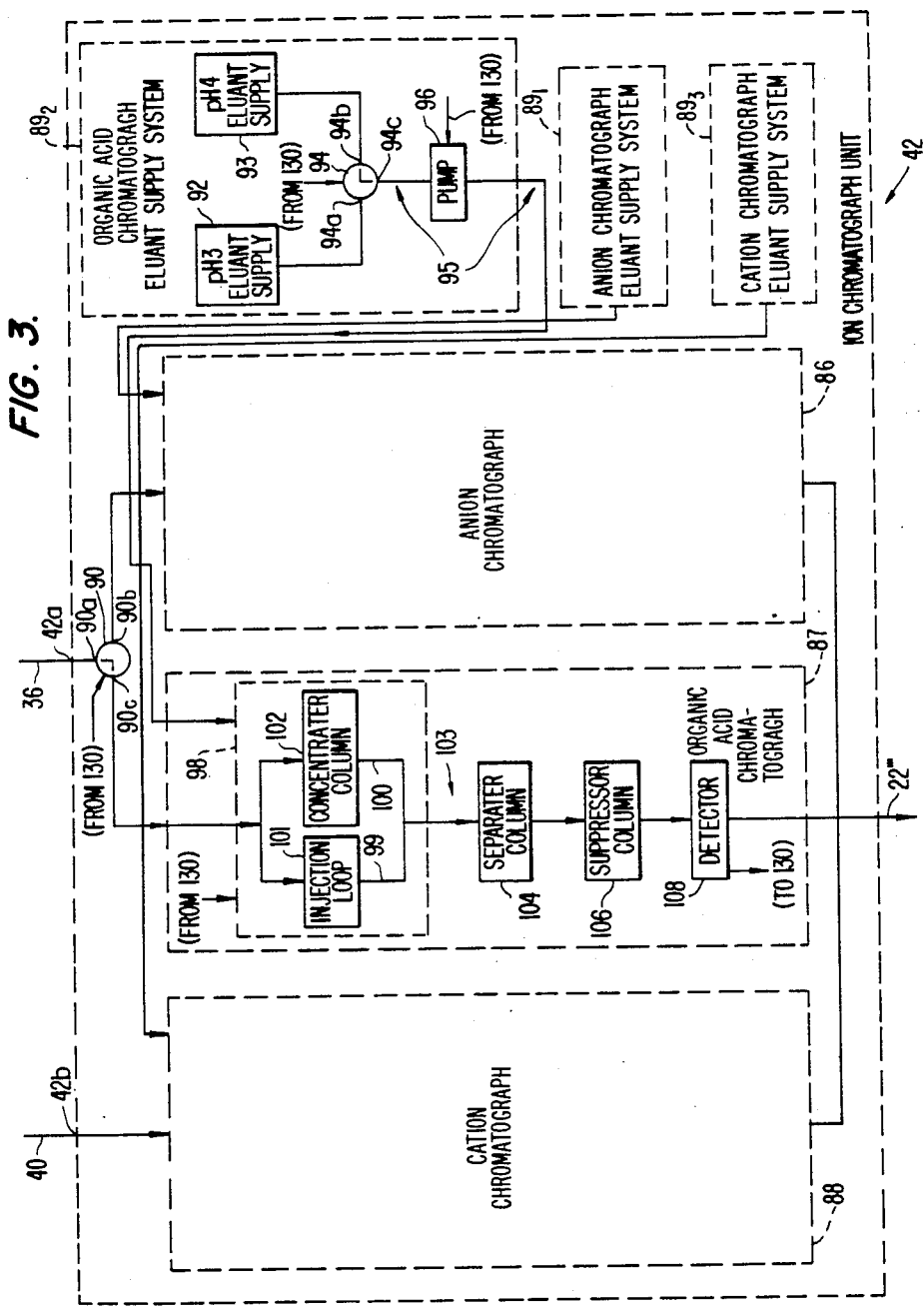
FIG. 3 is a simplified block diagram of portions of an ion chromatograph unit.

The ion chromatograph unit 42 is illustrated in the simplified block diagram of FIG. 3. One example of the ion chromatograph unit 42 contemplated for use in the monitoring system of the present invention is a Dionex Model 8000 ion chromatograph. The ion chromatograph unit 42 comprises, for example, an anion chromatograph 86, an organic acid chromatograph 87, a cation chromatograph 88, an anion chromatograph eluant supply system $89_1$ an organic acid chromatograph eluant supply system $89_2$, and a cation chromatograph eluant supply system $89_3$. A chromatograph selector valve 90 has an input 90a for receiving one of the third influent fluid sample streams from the first input 42a of the ion chromatograph unit 42 and first and second outputs 90b and 90c in fluid communication with the anion chromatograph 86 and the organic acid chromatograph 87, respectively. A chromatograph selector valve actuation signal operates the chromatograph selector valve 90 between first and scond positions, the first position connecting the input 90a and the first output 90b thereof, and the second position connecting the input 90a and the second output 90c thereof. The chromatograph selector valve 90 is ordinarily in the first position to provide the third influent fluid sample stream to the anion chromatograph 86, and is selectively actuated to connect the input 42a with the organic acid chromatograph 87 only when it is determined that organic acid analysis is required, as described below. Organic acid chromatography is performed only when necessary since the suppressor column in the organic acid chromatograph 87 must be replaced relatively often, at a high cost. The cation chromatograph 88 receives one of the fourth fluid sample streams from the second input 42b of the ion chromatograph unit 42.

The anion, organic acid and cation chromatographs 86-88, and the anion, organic acid and cation chromatograph eluant supply systems $89_1$-$89_3$ include substantially similar, corresponding elements, and thus only the organic acid chromatograph 87 and the organic acid chromatograph eluant supply system $89_2$ are illustrated and described in detail.

The organic acid chromatograph eluant supply system $89_2$ comprises plural eluant supplies, for example, a pH 3 eluant supply 92 and a pH 4 eluant supply 93 for storing and supplying pH 3 and pH 4 eluants, respectively. An eluant selector valve 94 has first and second inputs 94a, 94b in fluid communication with respective ones of the eluant supplies 92, 93, and is actuable, in accordance with an eluant selector valve actuation signal, to provide a selected one of the eluants to its output 94c. An eluant supply line 95 connects an eluant pump 96 to receive the output of the eluant selector valve 94. The eluant pump 96 supplies the selected eluant to each of the chromatographs 86-88 at a predetermined volumetric rate via the eluant supply line 95, in accordance with an eluant volume actuation signal.

Whereas the organic acid chromatograph eluant supply system $89_2$ supplies plural eluants, the anion and cation chromatograph eluant supply systems $89_1$, $89_3$ only provide a single eluant; thus, the anion and cation chromatograph eluant supply systems $89_1$, $89_3$ do not require a selector valve. The eluant supplied to the anion chromatograph 86 is a mixture of carbonate and bicarbonate and the eluant supplied to the cation chromatograph 88 is hydrochloric acid HCl or nitric acid $HNO_3$.

The organic acid chromatograph unit 87 comprises a sample volume control unit 98 which prepares a sample volume of the third fluid sample stream being supplied to the first input 42a of the ion chromatograph unit 42 for analysis by the organic acid chromatograph 87. The sample volume control unit 98 basically includes first and second parallel fluid lines 99, 100, an injection loop 101 and a concentrator column 102. Further details of the sample volume control unit 98 are illustrated in and explained with respect to FIG. 5. The organic acid chromatograph unit 87 also comprises a chromatograph fluid line 103, which connects a separator column 104, a suppressor column 106 and a detector 108 in a fluid series circuit.

An example of the strength of the integrated monitoring system of the present invention is the placement of the cation conductivity monitors 32 ahead of, or upstream from, the ion chromatograph unit 42. Ammonia, which is present at relatively high concentrations in most power plant steam cycle water, causes problems in the detection of anions by the anion chromatograph 86. By supplying the third influent fluid sample streams to the cation conductivity montiors 32, which remove cations including ammonia from a fluid sample, prior to supplying one of the third influent fluid sample stream to the anion chromatograph 86, ammonia is removed from the third influent fluid sample stream before it is supplied to the anion chromatograph 86, thereby eliminating this serious problem.

Figure 4:
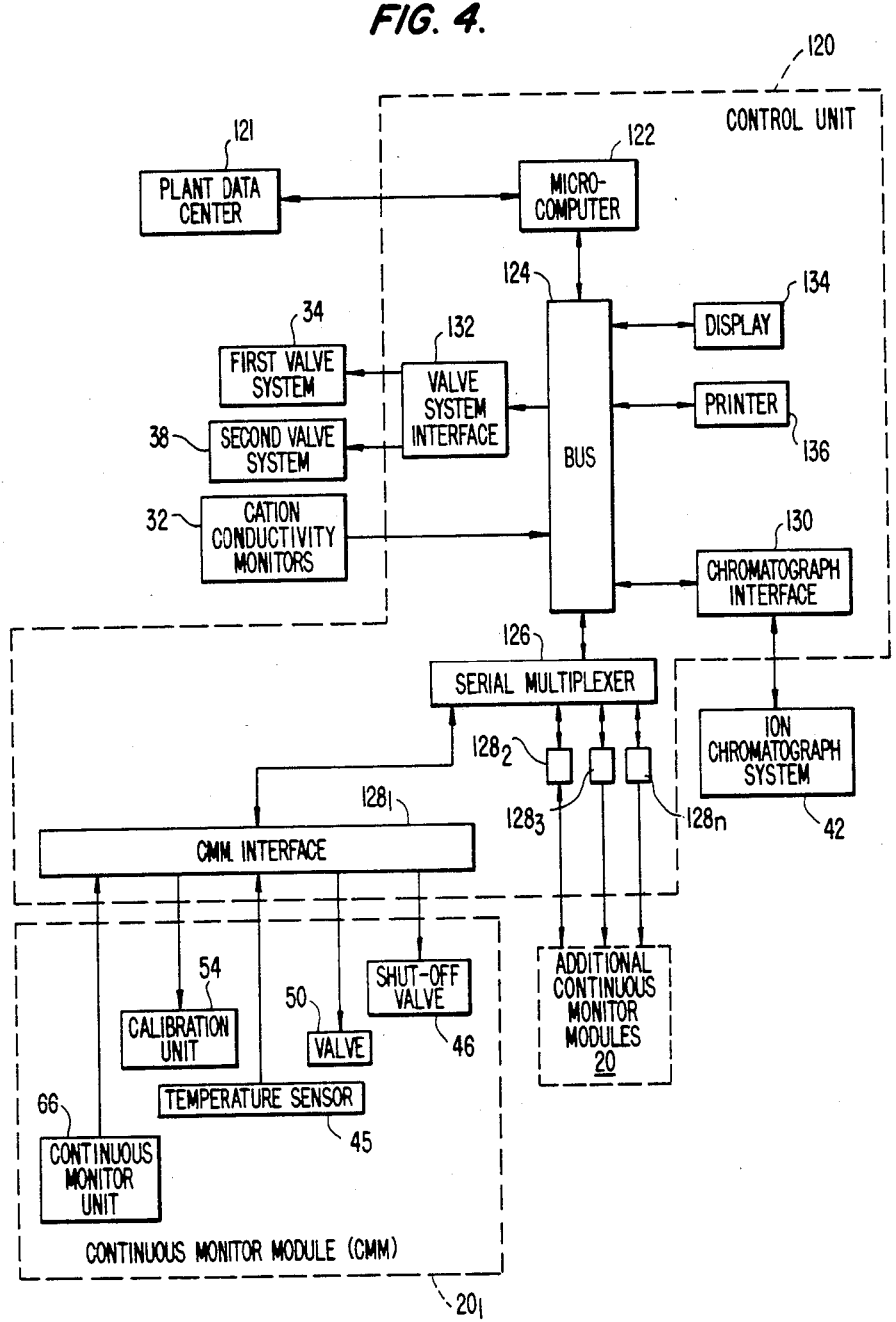
FIG. 4 is a schematic diagram of the monitoring system of the present invention.

FIG. 4 is a schematic diagram illustrating a control unit 120 which interfaces with the continuous monitor modules 20, the cation conductivity monitors 32, the first and second valve systems 34, 38, and the ion chromatograph unit 42, as well as a power plant data center 121, to provide fully automatic water chemistry monitoring and calibration functions and to interface with overall plant operation. The control unit 120 includes a microcomputer 122, a data bus 124, a serial multiplexer 126, a plurality of continuous monitor module (CMM) interfaces 128, individually designated $128_1$, $128_2$, ... $128_n$, corresponding to respective ones of the continuous monitor modules 20, a chomatograph interface 130, a valve system interface 132, a display 134, and a printer 136. The bus 124 receives control signals generated by the microcomputer 122 and supplies the control signals to the valve system interface 132, the CMM interfaces 128 via the serial multiplexer 93, and the chromatograph interface 130. Each CMM interface 128 may be, for example, Martek interface module, Model Mark XX, for receiving the temperature signals from temperature sensor 45 and the continuous monitor signals from continuous monitor unit 66, and providing actuator signals to shutoff valve 46, valve 50 and calibration unit 54.

The control signals generated by the microcomputer 122 include calibration control signals, eluant supply control signals, sample volume control unit control signals for each of the chromatographs 86-88, chromatograph selector means control signals and first and second valve system control signals. These control signals are converted to corresponding actuator signals by the CMM interfaces 128, the chromatograph interface 130 and the valve system interface 132, each of which functions as a decoder/driver to generate the actuator signals necessary to operate the various valves and pumps at the appropriate voltages. The bus 124 also receives the chromatograph signals via the chromatograph interface 130 and the temperature signals and the continuous monitor signals generated by each continuous monitor module 20 via corresonding CMM interfaces 128 and the serial multiplexer 126 and supplies these signals to the microcomputer 122.

Figure 5:
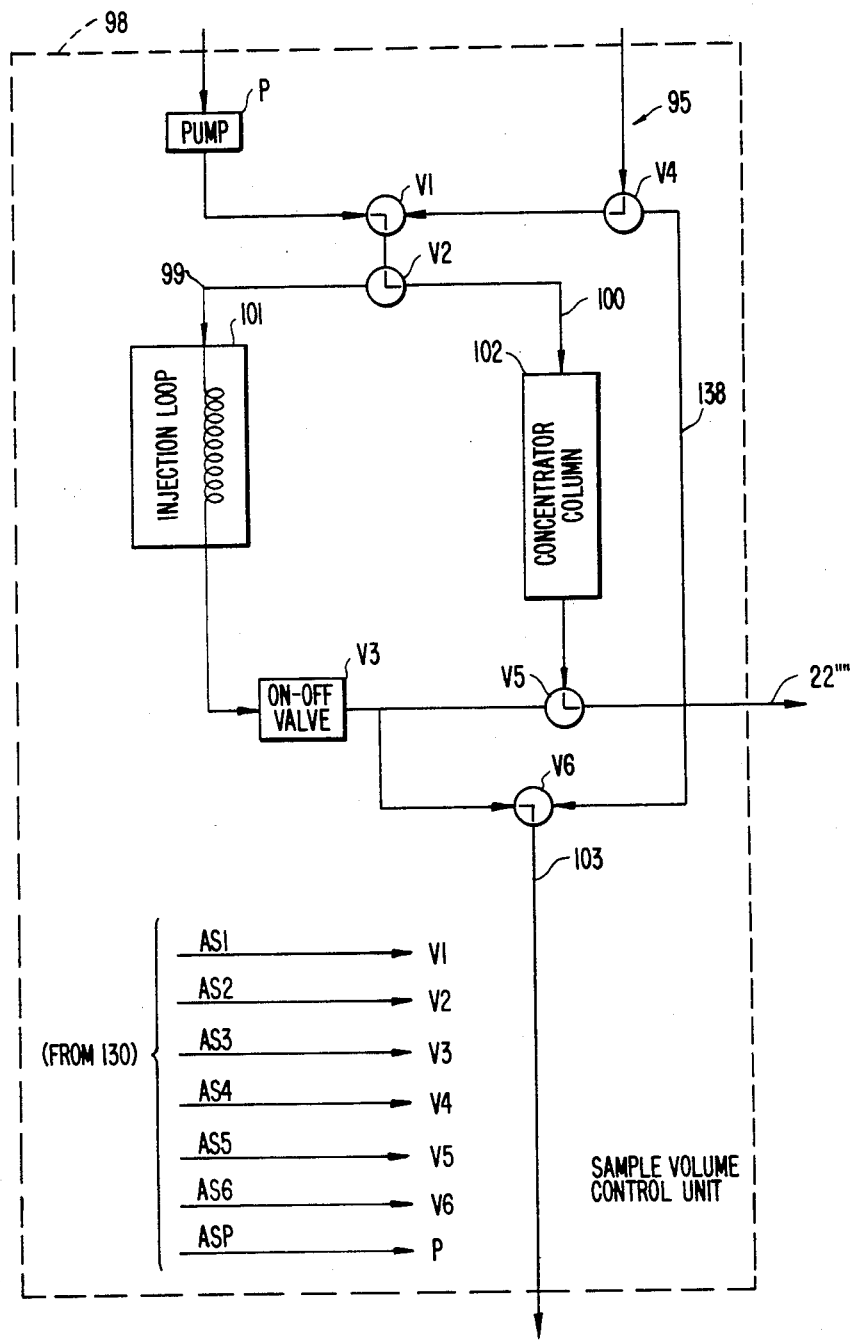
FIG. 5 is a diagram of a sample volume control unit of one chromatograph in the ion chromatograph unit in FIG. 3.

FIG. 5 is a block diagram of a standard valve arrangement employed in the sample volume control unit 98 to prepare a sample volume of an influent fluid sample stream for analysis. The sample volume control unit 98 comprises a pump P for supplying the influent fluid sample stream at a predetermined volumetric rate in accordance with an activation signal ASP, and valves V1-V6 selectively operable in accordance with actuation signals AS1-AS6 to establish one of five flow paths FP1-FP5: the first flow path FP1 extends from the pump P through the injector loop 101 to valve V3; the second flow path FP2 extends from the pump P through the concentrator column 102 to a drain 22''''; the third flow path FP3 extends from the eluant supply line 95 through the injection loop 101 to the separator column 104; the fourth flow path FP4 extends from the eluant supply line 95 through the concentrator column 102 to the separator column 104; and the fifth flow path FP5 extends from the eluant supply line 95 to the separator column 104. The pump P provides the influent fluid samples stream at a known volumetric rate of flow and the pump 96 in the eluant supply system 89 provides the eluant at a known volumetric rate of flow so that control of the valves V1-V6 to establish flow paths FP-1-FP-5, and control of pump P and pump 96 as a function of time provides a specific volume of an influent fluid sample stream or an eluant. Actuation signals AS1-AS6 and ASP comprise sample volume control means actuator signals.

Upon a determination that the calculated, required volume of the influent fluid sample to be prepared for analysis, the "sample volume", is the injection loop volume, the injection loop volume being defined as the combined volume of the first parallel fluid line 99 and the injection loop 101, actuation signals AS1-AS6 are generated to establish flow path FP1. In particular, actuation signals AS1 and AS2 are generated to actuate valves V1 and V2 to provide the influent fluid sample stream to the injection loop 101, and actuation signal AS3 is generated to close valve V3. Then, actuation signal ASP is generated to operate pump P until the injection loop 101 and the first parallel fluid line 99 are filled with the influent fluid sample. Of course, the time necessary to fill the injection loop 101 and the first parallel fluid line 99 can be calculated from the known injection loop volume and the known volumetric flow rate provided by pump P. After the injection loop 101 and the first parallel fluid line 99 are filled with the influent fluid sample actuation signals AS1, AS4 and AS6 are generated to establish flow path FP3, and then actuation signal AS3 is generated to open valve V3 and pump 96 is actuated so that an eluant moves the sample volume of the influent fluid sample, which is equal to the injection loop volume, through the separator column 104, the suppressor column 106, and the detector 108.

Upon a determination that the sample volume is greater than the injection loop volume, but limited to a maximum load value, valves V1–V6 are operated to sequentially establish flow paths FP2 and FP4. First, actuation signal AS3 is generated to close valve and V3, Then, actuation signals AS1, AS2, and AS5 are generated to operate valves V1, V2, and V5 to supply the influent fluid sample stream to the concentrator column 102 and then to the drain 22'''', thereby establishing flow path FP2. After flow path FP2 has been established, actuation signal ASP is generated to operate pump P for a time which provides the sample volume of the influent fluid sample stream. In this manner the sample volume of influent fluid sample stream is passed through the concentrator column 102 and the ions in the influent fluid sample stream are collected in a resin (not shown) in the concentrator column 102. When the ions from the predetermined volume of the influent fluid sample have been collected in the resin, actuator signals AS1, AS4 and AS5 are generated to actuate valves V1, V4 and V5 to establish flow path FP4 and the pump 96 is actuated to supply an eluant through eluant supply line 95 at a predetermined volumetric rate. The eluant passes through the resin in the concentrator column 102 and carries the ions accumulated in the resin to the separator column 104, the suppressor column 106 and the detector 108.

If it is desired to supply an eluant directly to the separator column 104, actuation signals AS4 and AS6 are generated to establish flow path FP5. Then, pump 96 is actuated to supply an eluant through supply line 95, supply line 138, and chromatograph fluid line 103 to the separator column 104.

The operation of the continuous on-line water chemistry monitor system of the present invention will be described with reference to the flowcharts in FIGS. 6–15.

Figure 6A:
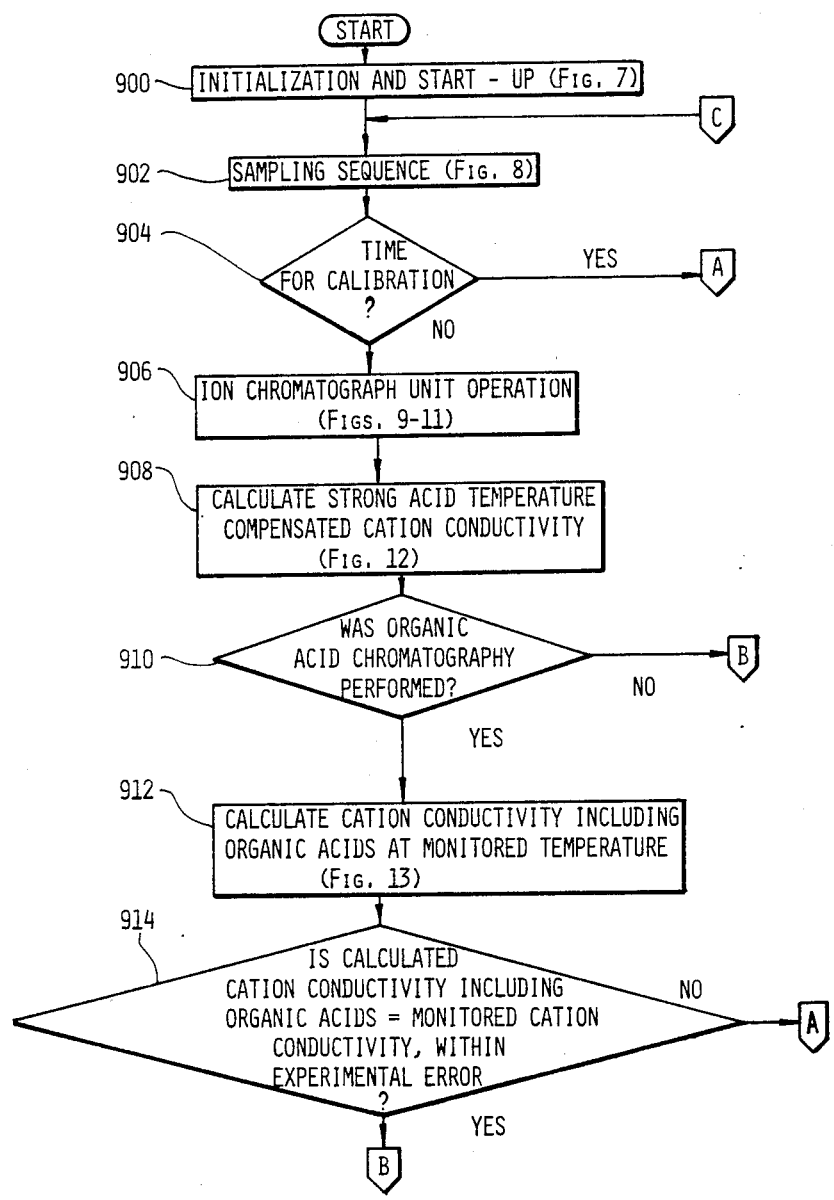
FIGS. 6A and B-15 are flowcharts for describing the operation of the monitoring system of the present invention.
Figure 6B:
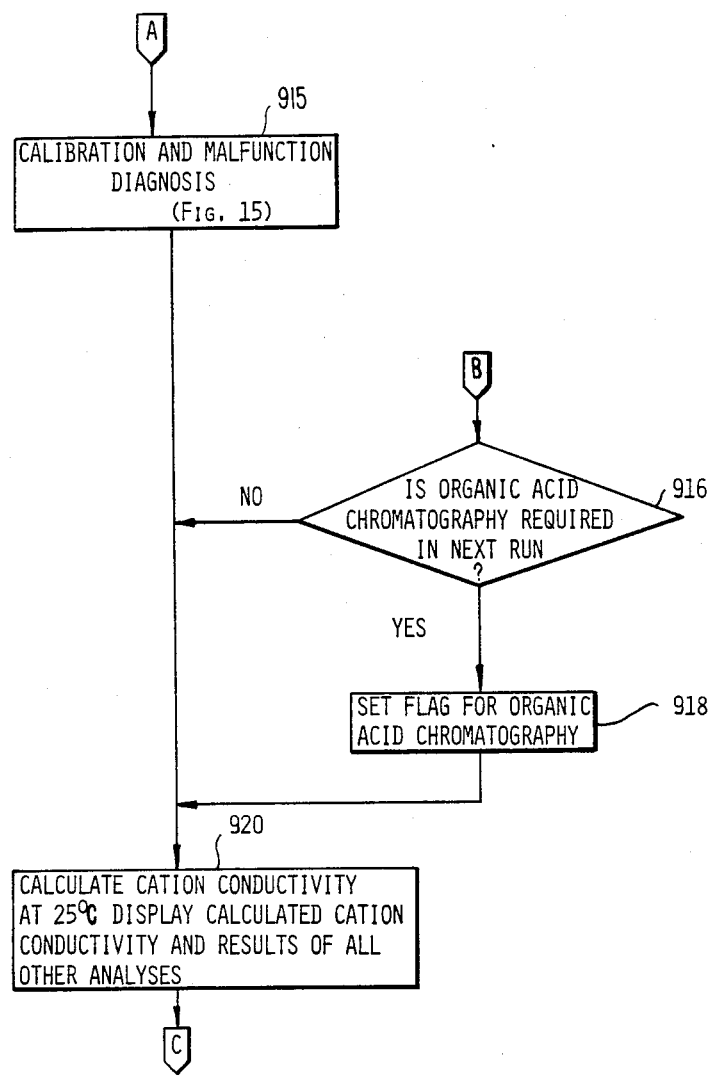

FIGS. 6A and 6B are flowcharts showing the overall operation of the system of the present invention.

Step 900: Initialization and start-up of the system, including selecting analyses to be performed in the initial run, as shown in detail in FIG. 7.

Step 902: Determination of the sampling sequence for the first and second valve systems 34, 38, i.e., the order in which the first and second valve systems 34, 38 supply the third and fourth influent fluid sample streams to the ion chromatograph unit 42, as shown in detail in FIG. 8.

Step 904: Determine if a predetermined calibration interval has elapsed. If the calibration interval has elapsed, calibration is to be performed and processing proceeds to step 915. If calibration is not to be performed, processing proceeds to step 906.

Step 906: Operation of the ion chromatograph unit 42 to perform anion chromatography, organic acid chromatography, and cation chromotography, as shown in detail in FIGS. 9–11.

Step 908: Calculation of a strong acid temperature compensated cation conductivity based on the monitored temperature of the influent fluid sample stream analyzed by the ion chromatograph unit, predetermined conductivity equations, and the ions detected by anion chromatography and cation chromatography.

Step 910: Determine if organic acid chromatography was performed.

Step 912: If organic acid chromatography was performed, calculate cation conductivity including organic acids at the monitored temperature, as shown in detail in FIG. 13.

Step 914: Determine if the calculated cation conductivity including organic acids is approximately equal to the monitored conductivity. If these two values do not correspond within experimental error, processing proceeds to step 905 for calibration. If these valves do not correspond, processing proceeds to step 915; if these values do correspond, processing proceeds to step 916.

Step 915: If it is determined, in step 904, that calibration is to be performed, calibration and malfunction diagnoses are performed, as shown in detail in FIG. 15.

Step 916: Determine if organic acid chromatography is required in the subsequent run by comparing the strong acid temperature compensated cation conductivity with the monitored cation conductivity. If these valves are not approximately equal, it is determined that organic acid chromatography is to be performed on the next third influent fluid sample stream to be supplied to the ion chromatograph unit 42.

Step 918: If organic acid chromatography is determined to be required in the next run, a flag is set for organic acid chromatography.

Step 920: A cation conductivity for 25° C. is calculated, and the calculated conductivity at 25° C. and the results of all other analyses are displayed. Processing then returns to step 902.

Figure 7:
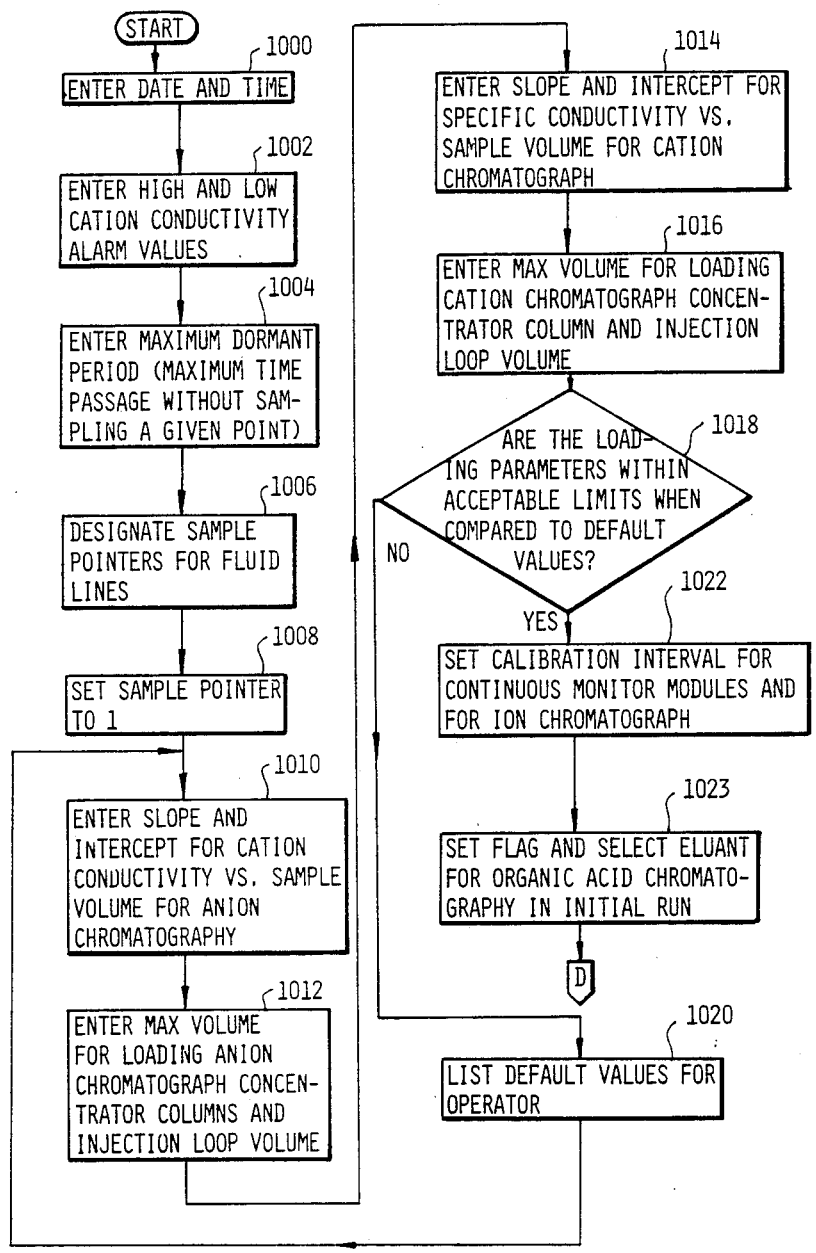

FIGS. 7–15 are flowcharts detailing the operations shown in the flow chart of FIG. 6. In particular, FIG. 7 is a flow chart illustrating the initialization and start-up procedure.

Step 1000: Enter date and time.

Step 1002: Enter high and low cation conductivity alarm values.

Step 1004: Enter maximum dormant period, i.e., the maximum time between ion chromatographic analysis of the influent fluid sample stream supplied by a particular one of the fluid lines 10. The maximum dormant period may be set at, for example, one day (24 hours).

Although the maximum period between the ion chromatograph analyses of a particular sample may be as long as 24 hours, the continuous monitors 68–73 in each continuous monitor module 20, as well as the cation conductivity monitors 32, provide continuous on-line monitoring of each influent fluid sample stream. Further, it is unlikely that the maximum dormant period will elpase between chromatographic analyses of a particular influent fluid sample stream since the time necessary for each run of the ion chromatograph unit 42 is approximately one half hour.

Step 1006: Designate sample pointers with corresponding fluid lines $10_1, 10_2, \ldots 10_n$.

Step 1008: Set sample pointer to 1.

Step 1010: Enter slope and intercept values from known equation describing to the relationship between the cation conductivity and the concentration of anions and organic acids in a fluid sample. This equation is used to determine the volume of a fluid sample necessary to provide the quantity of anions or organic acids which are necessary for accurate chromatographic analysis, i.e., the "sample volume" for the anion chromatograph 86.

Step 1012: Enter maximum volume for loading the anion chromatograph concentrator column 102. Enter the injection loop volume for the anion chromatograph 86.

Step 1014: Enter slope and intercept values for known equation describing the relationship of the specific conductivity and the concentration of cations in a fluid sample. This equation is used to determine the volume of a fluid sample necessary to provide the quantity of cations necessary for accurate cation chromatography, i.e., the "sample volume" for the cation chromatograph.

Step 1016: Enter maximum volume for loading cation chromatography concentrator column. Enter the injection loop volume for the cation chromatograph 88.

Step 1018: Determine if the maximum loading volumes and injection loop volumes for all chromatographs 86-88 are within acceptable limits when compared to default values.

Step 1020: List default values on display or printer 96, shown in FIG. 4, if the loading parameters are not within the acceptable limits when compared with default values and return to step 1010.

Step 1022: Set calibration interval for continuous monitor modules 20 and for the ion chromatograph unit 42.

Step 1023: Set flag and select eluant for organic acid analysis in initial run, and proceed to flow D (FIG. 8).

Figure 8:
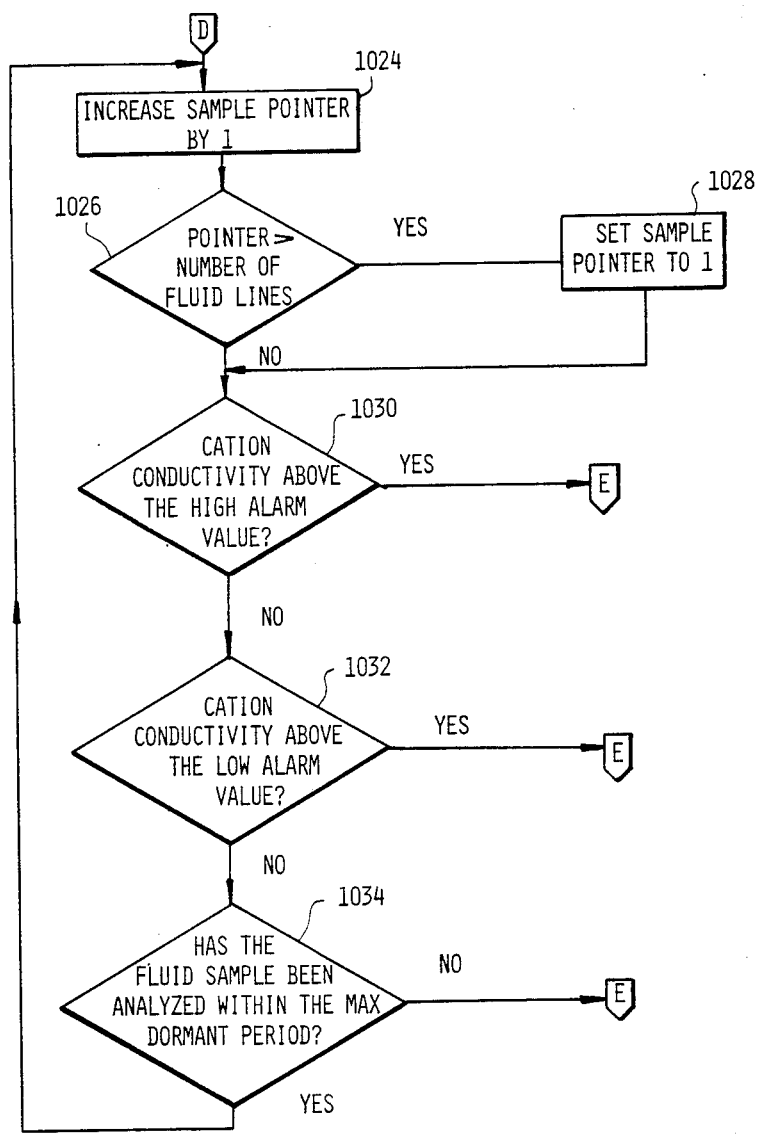

FIG. 8 is a flowchart describing the determination of the sequence in which the influent fluid sample streams, supplied by each of the fluid lines 10, are provided to the ion chromatograph unit Step 1024: Increase sample pointer by 1.

Step 1026: Determine if sample pointer value is greater than the number n of fluid lines 10.

Step 1028: Set pointer to 1 if the pointer valve is greater than the number n of fluid lines 10. From this point processing is performed for the influent fluid sample stream supplied by the fluid line 10 corresponding to the sample pointer valve.

Step 1030: Determine if the monitored cation conductivity is above the high alarm value set in step 1002. If the monitored cation conductivity value is above the high alarm value processing proceeds to flow E (FIG. 9).

Step 1032: Determine if the monitored cation conductivity is above the low alarm value. If the cation conductivity is above the low alarm value, processing proceeds to flow E. If the cation conductivity is not above the low alarm value, it is determined that the influent fluid sample stream does not contain a high enough concentration of ions to justify performing chromatographic analysis.

Step 1034: Determine if the influent fluid sample stream associated with the selected fluid line 10 has been analyzed within the maximum dormant period set in step 1004. If the fluid sample has not been analyzed within the maximum dormant period, processing proceeds to flow E. If the fluid sample has been analyzed within the maximum dormant period, processing returns to step 1024.

Figure 9:
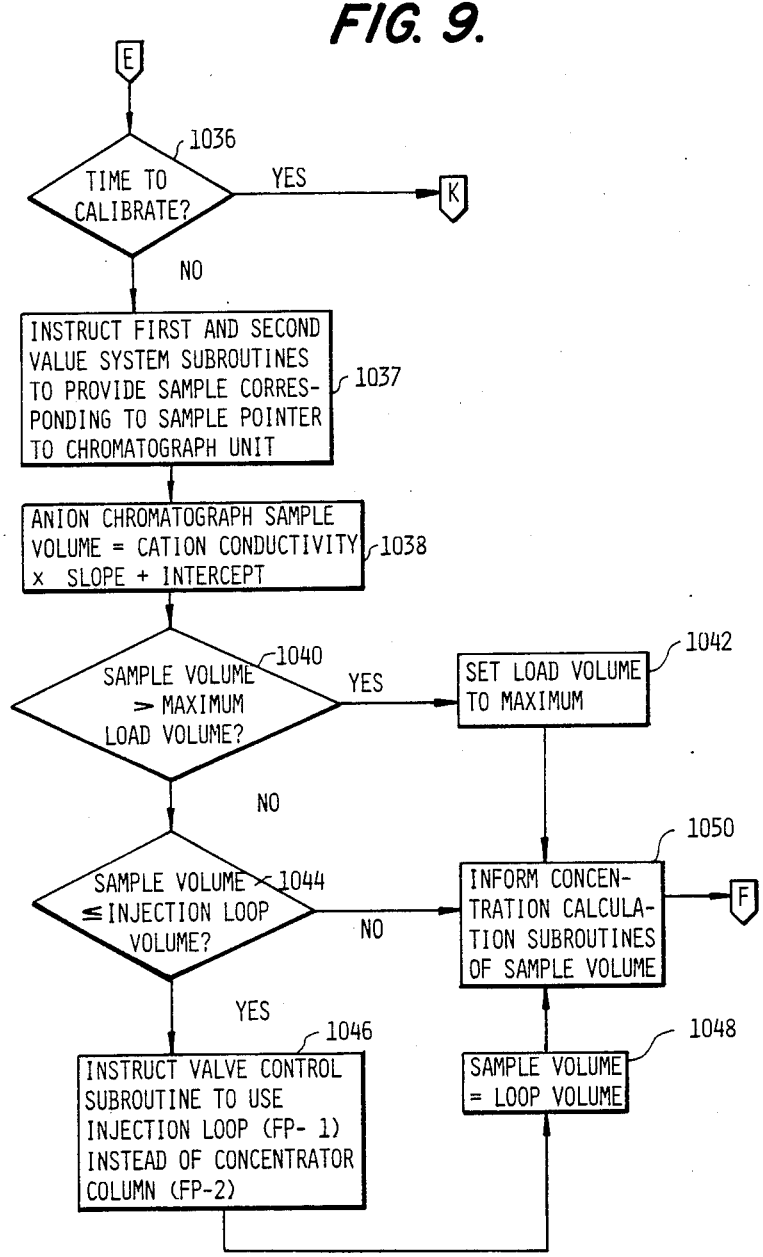
Figure 10:
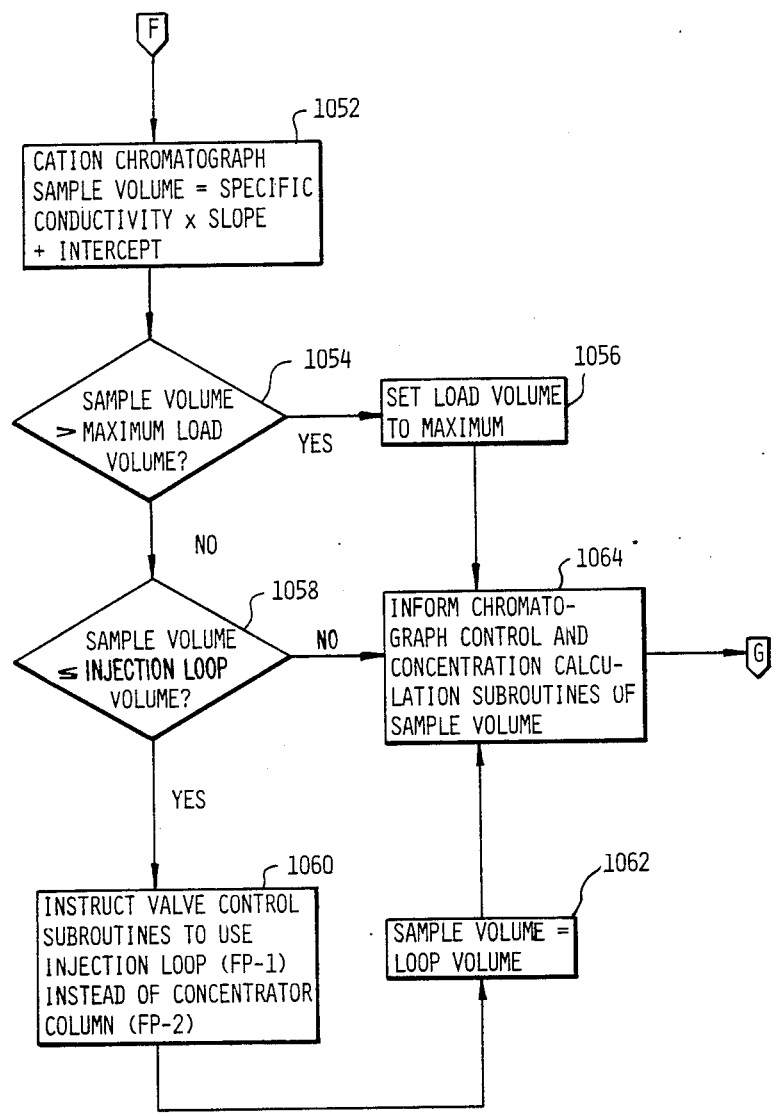
Figure 11:
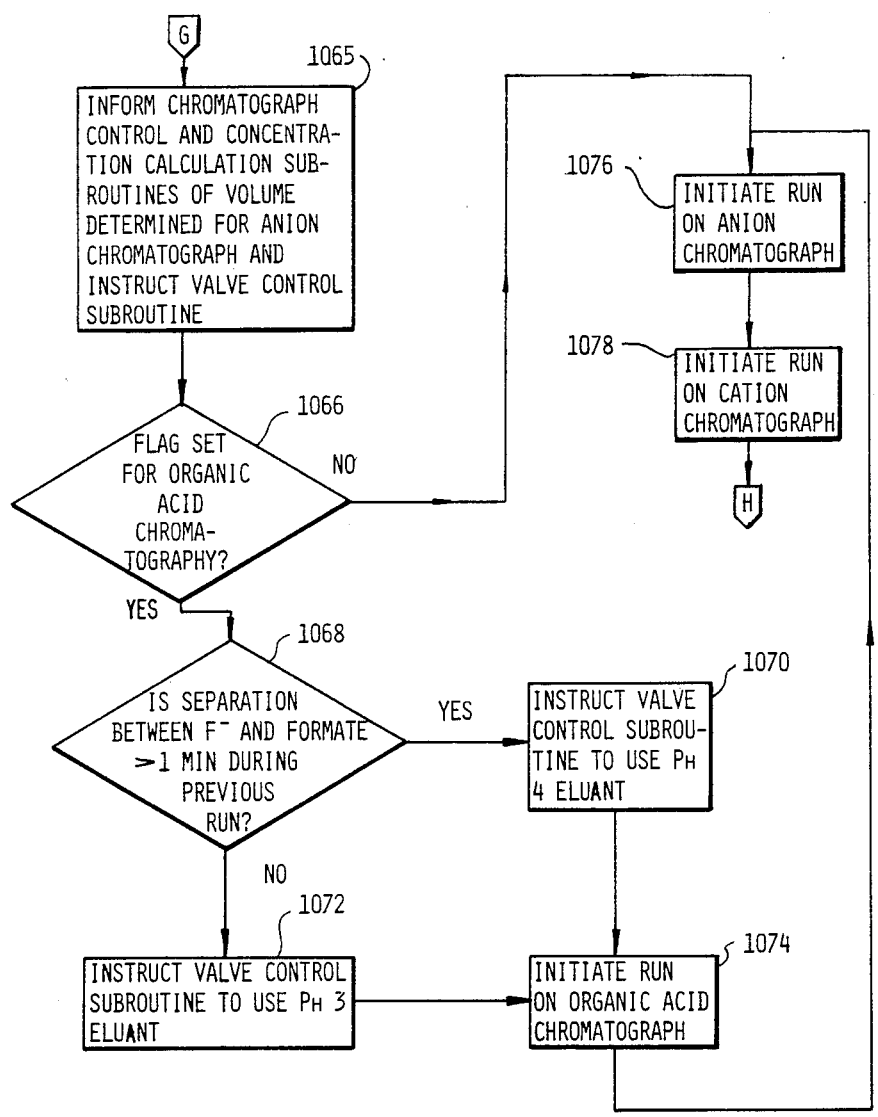

The flow charts of FIGS. 9-11 provide an illustration of the control of the operation of the ion chromatograph unit 42.

Step 1036: Determine if the calibration interval has elapsed. If the interval has elapsed, processing proceeds to flow K, shown in FIG. 15, for calibration.

Step 1037: Instruct first and second valve system subroutines to provide the third and fourth fluid sample streams corresponding to the influent fluid sample stream supplied by the fluid line 10 corresponding to the sample pointer to the ion chromatograph unit 42. The first and second valve system subroutines can be generated by one of ordinary skill in the art in accordance with the disclosure in U.S. Pat. No. 4,414,858, previously incorporated by reference.

Step 1038: Calculate an anion chromatograph sample volume with predetermined equations, particularly by multiplying the monitored cation conductivity with the slope entered in step 1010 and then adding the intercept value entered in step 1010.

Step 1040: Determine if the calculated sample volume is greater than the maximum load volume for the anion chromatograph concentrator column entered in step 1012. If the calculated sample volume is greater than the maximum load volume, processing proceeds to step 1042; otherwise, processing proceeds to step 1044.

Step 1042: Set anion chromatograph sample volume to the maximum load volume if the calculated sample volume is greater than the maximum load volume, then proceed to step 1050.

Step 1044: Determine if the calculated sample volume is less than or equal to the injection loop volume set in step 1012. If the calculated sample volume is greater than the injection loop volume, processing proceeds to step 1050. If the calculated sample volume is less than or equal to the injection loop volume, processing proceeds to step 1046.

Step 1046: Instruct a valve control subroutine for the anion chromatograph 86 sample volume control unit 98 to use the injection loop 101 (FP-1) instead of the concentrator column 102 (FP-2), if the calculated sample volume is less than or equal to injection loop volume. The valve control subroutine can easily be developed by one of ordinary skill in the art in accordance with the description of the operation of the sample volume control unit 98 previously provided.

Step 1048: Set sample volume to the loop volume.

Step 1050: Inform concentration calculation subroutines of the sample volume, i.e., the calculated sample volume if it is greater than the injection loop volume and less than the maximum load volume, the maximum load volume set in step 1042 if the calculated sample volume is greater than the maximum load volume, or the loop volume set in step 1048 if the calculated sample volume is less than or equal to the injection loop volume. The concentration calculation subroutines can be developed by one of ordinary skill in the art based on the operation of standard chromtographs. After the anion chromatograph sample volume is determined, processing proceeds to flow F (FIG. 10).

Step 1052: Calculate cation chromatograph sample volume with predetermined equations, particularly by multiplying the monitored specific conductivity with the slope entered in step 1014 and then adding the intercept valve entered in step 1014.

Step 1054: Determine if the calculated cation chromatograph sample volume is greater than the maximum load volume set in step 1016. If the calculated sample volume is grater than the maximum load volume, processing proceeds to step 1056; otherwise, processing proceeds to step 1058.

Step 1056: Set cation chromatograph sample volume to maximum load volume if the calculated sample volume is greater than the maximum load volume.

Step 1058: Determine if the calculated sample volume is less than or equal to the injection loop volume set in step 1016.

Step 1060: Instruct cation chromatograph sample volume control unit (not shown) valve control subroutine to use an injection loop (FP-1) instead of a concentrator column (FP-2), if the calculated sample volume is less than or equal to the injection loop volume.

Step 1062: Set sample volume to the injection loop volume.

Step 1064: Inform concentration calculation subroutine of the sample volume. After the cation chromatograph sample volume is determined, processing proceeds to flow G (FIG. 11).

Step 1065: Set the organic acid chromatograph sample volume to the anion chromatograph sample volume and instruct valve control and concentration calculation subroutines accordingly.

Figure 14:
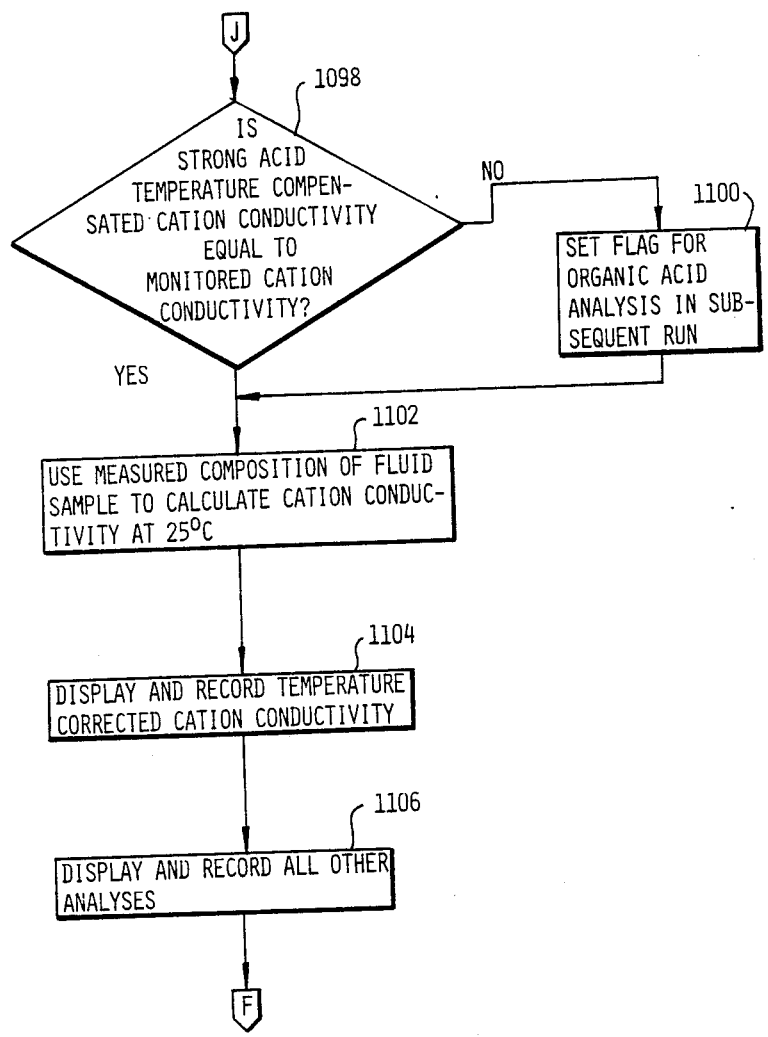

Step 1066: Determine if the flag is set for an organic acid analysis. For the initial run, the flag is set in step 1023, and for subsequent runs the flag for organic acid analysis is set in the processing of flow J (FIG. 14). If the organic acid analysis flag is not set, processing proceeds to step 1076.

Step 1068: Determine if the time for the separation of flouride (F$^-$) and formate (an anion often found in power plant steam cycle water) which occurs in the organic acid chromatograph separator column (not shown), is greater than one minute during the previous run of the organic acid chromatograph 87 in order to select the appropriate eluant. In the initial run the eluant is selected in step 1023. The separation time is determined by the order of the peaks for flouride and formate in the analysis of the previous run, and one of ordinary skill in the art would be able to instruct the control system to determine the order of the peaks automatically.

Step 1070: If the separation time during the previous run was greater than one minute, a valve control subroutine for the eluant supply system 89 is instructed to supply a pH 4 eluant. One of ordinary skill in the art would be able to develop a valve control subroutine for acuating the eluant selector valve 94 to select a pH 3 or pH 4 eluant.

Step 1072: If the separation time during the previous run was one minute or less, the valve control subroutine for the eluant supply system 89 is instructed to supply a pH 3 eluant.

Step 1074: Initiate organic acid chromatography.

Step 1076: Initiate anion chromatography.

Step 1078: Initiate cation chromatography and then proceed to flow H (FIG. 12).

Figure 12:
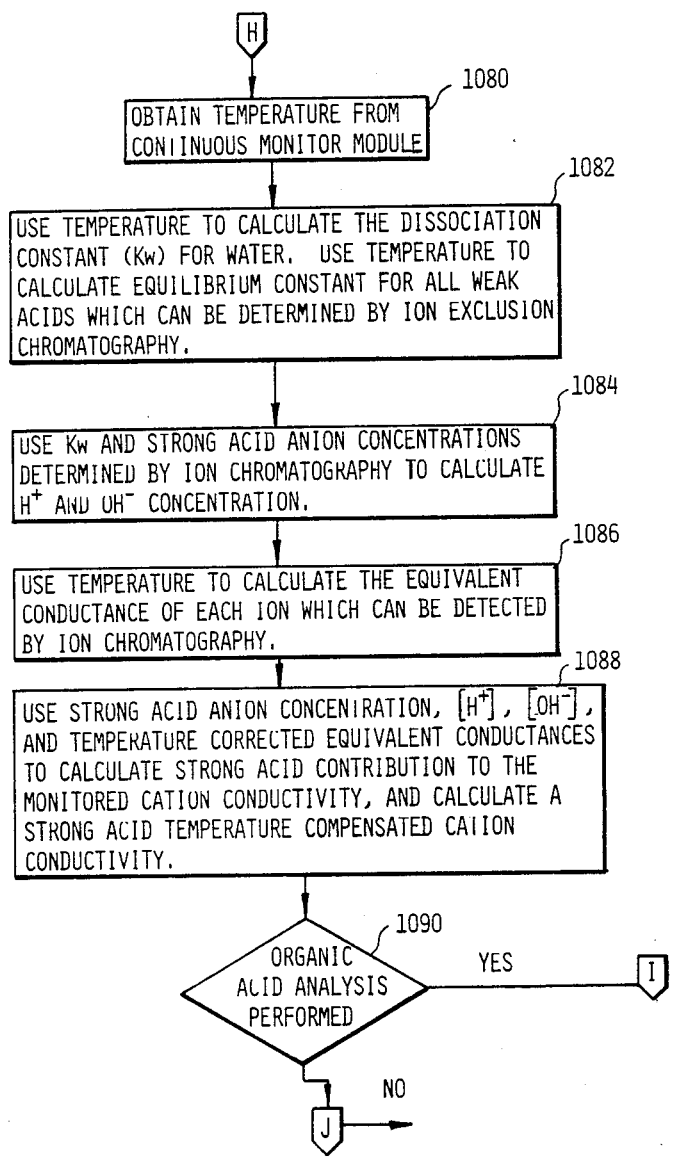

The flow chart of FIG. 12 relates to the calculation of a strong acid temperature compensated cation conductivity using predetermined conductivity equations.

Step 1080: Obtain the monitored temperature of the fluid sample undergoing chromatographic analayis from the corresponding continuous monitor module 20.

Step 1082: Calculate the dissociation constant for water (Kw) using the monitored temperature obtained in step 1080 and a value obtained from a computer resident look-up table based on data presented in a table of Ionization Constants for water (Kw) presented in the Handbook of Chemistry and Physics, 56th Ed., (CRC Press, Cleveland 1975), page D-152. Calculate the equilibrium, or inonization constants for all weak acids which can be determined by ion exclusion chromatography using the monitored temperature and values obtained from a computer resident look-up table based on data presented in a table of Ionization Constants of Acids in Water at Various Temperatures presented in the Handbook of Chemistry and Physics at page D-152.

Step 1084: Calculate H$^+$ and OH$^-$ concentrations using the dissociation constant Kw and strong acid anion concentrations determined by ion chromatography by solving the following equations (1)-(5) simultaneously:

Equilibrium Equations $$K_w = [H^+][OH^-] \tag{1}$$

$$K_{Ai} = \frac{[H^+][A_i^-]}{[HA_i]} \tag{2}$$

wherein $K_w$ = is the equilibrium constant for water at the monitored termperature;

$K_{Ai}$ is the equilibrium contstant for the with weak acid, $HA_i$, which has been determined by organic acid chromatography;

[H$^+$] is the concentration of the hydrogen ion;

[$A_i^-$] is the concentration of the conjugate base of the ith acid, HA;

[$HA_i$] is the concentration of the ith acid, $HA_i$; and

[OH$^-$] is the concentration of the hydroxide ion.

Charge Balance Equation $$[H^+] = [OH^-] + \sum_{i=1}^{n} [A_i^-] + \sum_{j=1}^{m} [B_j^-] \tag{3}$$

wherein n is the number of weak acids determined by organic acid chromatograph; and m is the number of strong acid anion concentrations determined by ion chromatography.

Mass Balance Equations $$F_i = [HA_i] + [A_i^-] \tag{4}$$

$$F_j = [B_j^-]. \tag{5}$$

Step 1086: Calculate the equivalent conductance for each ion which can be detected by ion chromatography using the monitored temperature obtained in step 1080 and values obtained from a computer resident look-up table based on the data presented in a table of the Equivalent Conductance Separate Ions presented in the Handbook of Chemistry and Physics at page D-153.

Step 1088: Calculate the strong acid contribution to the monitored cation conductivity using strong acid anion concentrations, [H+], [OH−], and the temperature corrected equivalent conductances, and calculate a strong acid temperature compensated cation conductivity using the temperature corrected equivalent conductances and equation (6) below.

$$cc = [H^+]\lambda_{H^+} + [OH^-]\lambda_{OH^-} + \sum_{i=1}^{n}[A_i^-]\lambda_i + \sum_{i=1}^{m}[B_j^-]\lambda_j \quad (6)$$

wherein
- $cc$ is the cation conductivity;
- $\lambda_{H^+}$ is the equivalent conductance of the hydrogen ion;
- $\lambda_{OH^-}$ is the equivalent conductance of the hydroxide ion;
- $\lambda_i$ is the equivalent conductance of the conjugate base of the ith weak acid; and
- $\lambda_j$ is the equivalent conductance of the jth strong acid anion.

Since the concentrations of the weak acids determined by organic acid chromatograph are represented by $[A_i^-]$ and $[HA_i]$, only equations (1), (3) and (5) must be solved to calculate the strong acid anion concentrations for the strong acids determined by anion chromatography. Thus, to determine the strong acid anion concentrations, $[A_i^-]=0$ for all i.

To obtain the cation conductivity which includes both weak acid and strong acid anion concentrations, equation. (1)–(6) are solved simaltaneously for cc.

Step 1090: Determine if organic acid analysis was performed during the run. If organic acid analysis was performed processing proceeds to flow G, and if organic acid analysis was not performed, processing proceeds to flow I (FIG. 13).

Figure 13:
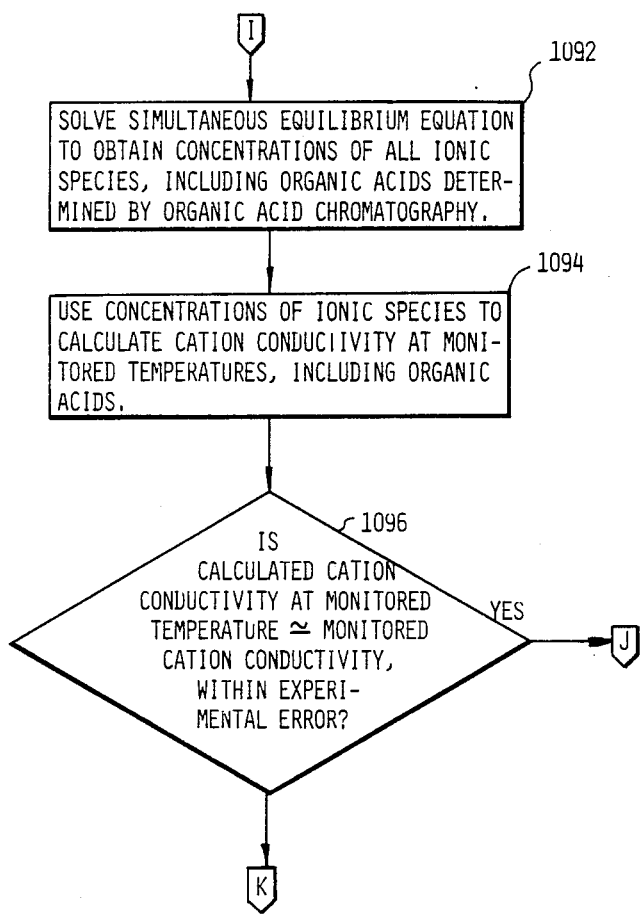

The flowchart of FIG. 13 relates to the calculation of a cation conductivity, including the organic acid concentrations determined by organic acid chromatography, at the monitored temperature.

Step 1092: Obtain concentrations of all of the ionic species, including organic acids, determined by ion chromatography by solving equations (1)–(5) including all Fi values obtained by organic acid chromatography.

Step 1094: Calculate cation conductivity at monitored temperature using concentrations of ionic species, including organic acids, obtained in step 1092.

Step 1096: Determine if the calculated cation conductivity at the monitored temperature, including organic acids, is approximately equal to the monitored cation conductivity, within the range of experimental error. If the calculated cation conductivity at the monitored temperature is not approximately equal to the monitored conductivity, processing proceeds to flow K (FIG. 15) for calibration. If the calculated cation conductivity at the monitored temperature is approximately equal to the monitored cation conductivity, processing proceeds to flow J (FIG. 14).

Step 1098: Determine if strong acid temperature compensated cation conductivity is approximately equal to the monitored cation conductivity. If these two values are not approximately equal, it is determined that organic acid analysis is required in the next, or subsequent, run and processing proceeds to step 1100; otherwise, processing proceeds to step 1102.

Step 1100: Set flag for organic acid analysis in subsequent run.

Step 1102: The measured composition of the sample fluid is used to calculate the cation conductivity at 25° C. This prediction is based on known parameters referenced in step 1082.

Step 1104: Display and record temperature corrected cation conductivity.

Step 1106: Display and record all other analytical results and proceed to flow D (FIG. 8) to perform subsequent run.

Figure 15:
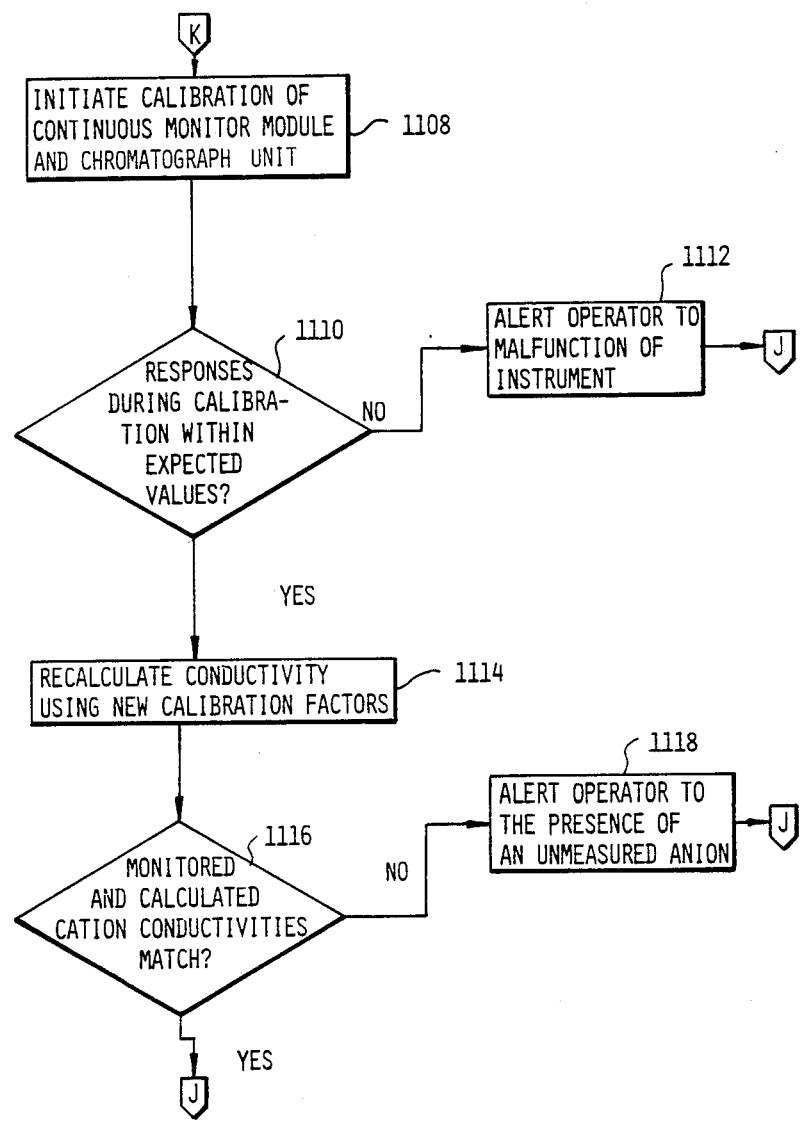

Flow K, shown in FIG. 15, relates to calibration and malfunction diagnosis.

Step 1108: If the calculated cation conductivity is not determined to be approximately equal to the detected conductivity at step 1096, the calibration subroutine is instructed to calibrate the continuous on-line monitors 68–73 in the continuous monitor module 20 corresponding to the influent fluid sample stream being analyzed during the run and the ion chromatograph unit 42.

Step 1110: Determine if the monitored chemical characteristics during calibration are within expected values, i.e., are the monitored chemical characteristics in the range of the predetermined chemical characteristics of the conditioned influent fluid sample stream.

Step 1112: If it is determined, at step 1110, that the chemical characteristic monitored by a particular instrument is not within the range of expected values during calibration, the operator is alerted of the malfunction of the particular instrument. The processing then proceeds to flow J (FIG. 14).

Step 1114: If the responses during calibration are all within the expected values, the cation conductivity is recalculated using the new calibration factors.

Step 1116: Determine if the monitored and calculated cation conductivities are approximately equal. If the conductivities are approximately equal, processing proceeds to flow J.

Step 1118: If the measured and calculated cation conductivities do not match, the operator is alerted of the presence of an unmeasured anion and processing continues to flow J.

The many features and advantages of the automatic continuous on-line monitoring system of the present invention will be apparent to those skilled in the art from the detailed specification. Further, since numerous modifications and changes will readily occur to those skilled in the art, the claims are intended to cover all suitable modifications and equivalents falling within the true spirit and scope of the invention.

We claim as our invention:

1. Apparatus for automatic, continuous on-line monitoring of a power plant steam cycle water system having a plurality of points where the chemical characteristics of the water in the system are to be measured, said water in the system at each said point having characteristic temperature conditions and cation conductivity levels in addition to said chemical characteristics, said apparatus comprising:

means at each point for extracting a respective extracted fluid sample stream to be monitored;

continuous monitor module means for each extracted fluid sample stream, each said continuous monitor module means comprising:

means for monitoring the temperature conditions of the corresponding extracted fluid sample stream and generating a temperature signal representative of the temperature conditions so monitored, calibration means for selectively conditioning the corresponding extracted fluid sample stream in accordance with calibration actuation signals, to provide a conditioned calibration stream having predetermined chemical characteristics for calibration of downstream components, first flow-splitter means for dividing said extracted fluid sample stream into first and second fluid sample streams, and means for continuous on-line monitoring of one or more selected chemical characteristics of said first fluid sample stream and generating continuous monitor signals representative of said one or more selected chemical characteristics so monitored;

second flow-splitter means for each of said second fluid sample streams for dividing the latter into respective third and fourth fluid sample streams;

means for monitoring the cation conductivity levels of each of said third fluid sample streams and generating corresponding cation conductivity signals representative of the cation conductivity levels so monitored;

ion chromatography means for on-line monitoring of one or more selected chemical characteristics of selected ones of said third and fourth fluid sample streams in accordance with chromatography actuation signals and generating chromatograph signals representative of the selected chemical characteristics so monitored by ion chromatography;

valve means selectively operable to supply a plurality of said third fluid sample streams and corresponding fourth fluid sample streams to said ion chromatograph means in individual succession, in accordance with a sampling sequence; and control means for:

receiving said temperature, continuous monitor, cation conductivity and chromatograph signals, determining said sampling sequence, calculating a derived cation conductivity for the fluid sample stream which corresponds to the third and fourth fluid sample streams being supplied to said ion chromatography means in accordance with predetermined conductivity equations, the temperature levels monitored in the fluid sample stream, and the selected chemical characteristics monitored by said ion chromatograph means, comparing said derived cation conductivity of the corresponding fluid sample stream with the cation conductivity levels monitored by the means for monitoring the cation conductivity levels, and using such comparison to choose which chemical characteristics are to be monitored by said ion chromatography means and to determine if calibration is necessary, selectively generating said calibration actuation signals at predetermined time intervals and between said predetermined time intervals, and generating said chromatograph actuation signals in accordance with the chemical characteristics selected by comparing said derived cation conductivity with the monitored cation conductivity levels.

2. Apparatus as set forth in claim 1, wherein:

said ion chromatograph means comprises:

anion chromatograph means for performing anion chromatography to monitor anions in said third fluid sample stream, organic acid chromatograph means for performing organic acid chromatography to monitor organic acids in said third fluid sample stream, cation chromatograph means for performing cation chromatography to monitor cations in said fourth fluid sample stream, and chromatograph selector means operable to supply said third fluid sample stream alternatively to either said organic acid chromatograph means or said anion chromatograph means in accordance with said chromatograph actuation signal;

said chromatograph actuation signal comprises an anion chromatograph signal representative of the monitored anions, an organic acid chromatograph signal representative of the monitored organic acids, and a cation chromatograph signal representative of the monitored cations;

said control means calculates a derived cation conductivity comprising a strong acid temperature compensated cation conductivity in accordance with the anions and cations monitored by said anion and cation chromatographs, in which case said control means compares said derived strong acid temperature compensataed cation conductivity with the cation conductivity levels monitored by the means for monitoring to determine if organic acid chromatography is required and selectively generates said chromatograph actuation signal; and said control means calculates a derived cation conductivity comprising a cation conductivity including organic acids at the monitored temperature conditions in accordance with the anions, organic acids and cations monitored by said anion, organic acid, and cation chromatographs, in which case said control means compares said derived cation conductivity including organic acids at the monitored temperature conditions with said cation conductivity levels monitored by the means for monitoring to determine if calibration is required and selectively generates said calibration acutation signals.

3. Apparatus as set forth in claim 2, wherein:

said fluid sample streams each have a specific conductivity and each of the continuous on-line monitoring means comprises a specific conductivity monitor for monitoring the specific conductivity of the corresponding first fluid sample stream and generating specific conductivity signals representative of the specific conductivity so monitored;

said ion chromatograph means further comprises anion chromatograph eluant supply means, organic acid chromatograph eluant supply means, and cation chromatograph eluant supply means, each of said anion, organic acid and cation chromatograph eluant supply means supplying an eluant to a corresponding one said anion, organic acid, and cation chromatograph means in accordance with corresponding anion, organic acid and cation chromatograph eluant supply means actuation signals;

said anion, organic acid and cation chromatograph means each comprises sample volume control means for preparing a sample volume of an fluid sample stream for monitoring in accordance with corresponding anion, organic acid and cation chromatograph sample volume control means actuator signals, and a detector;

said control means generataes said anion, organic acid, and cation chromatograph eluant supply system actuation signals;

said control means calculates a sample volume of the third fluid sample stream to be prepared for monitoring by said anion and organic acid chromatographs sample volume control means in accordance with the cation conductivity of the third fluid sample stream being supplied to said ion chromatograph means and a predetermined equation relating cation conductivity to ion concentration in a fluid sample and generates said anion and organic acid chromatograph sample volume control means actuator signals in accordance with the calculated sample volume; and said control means calculates a sample volume of the fourth fluid sample stream to be prepared for monitoring by said cation chromatograph sample volume control means in accordance with the specific conductivity of the fourth fluid sample stream being supplied to said ion chromatograph means and a predetermined equation relating specific conductivity to ion concentration in a fluid sample and generates cation chromatograph sample volume control means actuator signals in accordance with the calculated sample volume.

4. Apparatus as set forth in claim 3, wherein:

each continuous monitor module conprises deionizer means for selectively deionizing the fluid sample stream to produce a deionized fluid sample stream in accordance with deionizer means actuation signals;

each calibration means comprises:
mixed standard supply means for supplying a mixed standard solution,
rinse supply means for supplying a rinse solution,
calibration selector means selectively operable between a first position for outputting said mixed standard solution and a second position of outputting said rinse solution, in accordance with a calibration selector means actuation signal,
means for injecting said output of said calibration selector means into a corresponding deionized fluid sample stream in accordance with a calibration volume actuation signal, said calibration selector means in said first position thereof, and said injecting means injecting said mixed standard solution into the corresponding deionized fluid sample stream to condition the corresponding deionized fluid sample stream and to provide a conditioned deionized stream having predetermined selected chemical characteristics, and said calibration selector means, in said second position thereof, and said injecting means injecting said rinse solution into the corresponding fluid sample stream to rinse said mixed standard solution from said injecting means;

said control means generates said deionizer means actuation signals;

said calibration actuation signals comprise said calibration selector means actuation signal and said calibration volume actuation signal; and said control means calibrates said continuous monitor signals, said cation conductivity signals, and said chromatograph signals in accordance with the predetermined selected chemical characteristics of the conditioned stream.

5. Apparatus as set forth in claim 4, wherein:

each said sample volume control means comprises an injecton loop having a loop volume, a concentrator column, a drain, valve means selectively operable for establishing one of four flow paths, and a pump selectively operable for supplying an influent fluid sample at a predetermined volumetric rate of flow, said valve means and said pump being operable in accordance with corresponding anion, organic acid, and cation chromatograph sample volume control means actuator signals, said first flow path supplying a fluid sample stream to said injection loop to fill the injection loop with a volume of the fluid sample stream corresponding to said loop volume, said second flow path supplying a fluid sample stream through said concentrator column to said drain, said third flow path supplying a corresponding eluant through said injection loop to said detector, and said fourth flow path supplying a corresponding eluant through said concentrator column to said detector;

said control means compares the calculated sample volume for each of said anion, organic acid and cation chromatograph means with corresponding maximum load volumes and sets each sample volume to the corresponding maximum load volume if the calculated sample volume is greater than or equal to the maximum load volume;

said control means compares the calculated sample volume for each of said anion, organic acid, and cation chromatograph means with a corresponding one of said loop volumes if the calculated volume is less than the corresponding maximum load volume, sets each sample volume to the corresponding loop volume if the sample volume is less than or equal to the corresponding loop volume and sets each sample volume to the corresponding calculated sample volume if the corresponding calculated sample volume is greater than said corresponding loop volume and less than said corresponding maximum load volume; and said control means generates anion, organic acid and cation chromatograph sample volume control means actuation signals to sequentially establish said first and third flow paths in corresponding ones of said anion, organic acid and cation chromatograph sample volume control means if the corresponding sample volume is set at the corresponding loop volume, to sequentially establish said second and fourth flow paths if the corresponding sample volume is greater than said corresponding loop volume, and to operate said pump when said first and second flow paths are established and generates said anion, organic acid and cation eluant supply means actuation signals when said third and fourth flow paths are established in corresponding ones of said anion, organic acid and cation chromatograph sample volume control means.

6. Apparatus as set forth in claim 5, wherein:

said control means comprises:
a microcomputer,
a bus, operatively connected to said microcomputer,
a display, operatively connected to said bus,
a printer, operatively connected to said bus, a chromatograph interface, operatively connected to said bus and said ion chromatograph means, a serial multiplexer, operatively connected to said bus, and a plurality of continuous monitor module means interfaces corresponding to respective ones of said continuous monitor module means, operatively connected to said serial multiplexer and respective ones of said continuous monitor module means;

said microcomputer generates deionizer means control signals, calibration control signals, and chromatograph control signals;

said chromatograph interface receives said chromatograph control signals and generates said chromatograph selector means actuation signal, said anion, organic acid and cation chromatograph sample volume control means actuation signals, and said anion, organic acid and cation chromatograph eluant supply means actuation signals in accordance with said chromatograph control signals; and each said continous monitor module means interface receives said deionizer means control signals and said calibration control signals and generates said deionizer means actuation signals and said calibration actuation signals in accordance with said deionizer means and calibration control signals.

7. Apparatus as set forth in claim 2, wherein each continuous on-line monitoring means comprises monitors for monitoring chemical characteristics selected from the group of sodium, dissolved oxygen, hydrazine, ammonia, pH, and specific conductivity and generates continuous monitor signals representative of the monitored chemical characteristics.

8. Apparatus as set forth in claim 1, wherein said control means compares the monitored cation conductivity of each third fluid sample stream with a cation conductivity alarm value and interrupts said sampling sequence if any of said monitored cation conductivities exceeds said cation conductivity alarm value to supply the sample stream having a monitored cation conductivity exceeding said cation conductivity alarm value to said ion chromatograph means.

9. Apparatus for automatic continuous on-line monitoring of a power plant steam cycle water system having a plurality of points where the chemical characteristics of the water in the system are to be measured, said water in the system at each said point containing anions, cations and organic acids and having characteristic temperature conditions, cation conductivity levels and specific conductivity levels in addition to said chemical characteristics, said apparatus comprising:

means at each point for extracting a respective extracted fluid sample stream of power plant steam cycle water;

continuous monitor module means for each extracted fluid sample stream, each said continuous monitor module means comprising:

a filter;

a temperature sensor for sensing the temperature conditions of the extracted fluid sample stream and generating a temperature signal representative of the temperature conditions so sensed, a flow meter for supplying said extracted fluid sample stream at a predetermined volumetric rate, deionizer means for selectively deionizing the corresponding extracted fluid sample stream to produce a deionized fluid sample stream in accordance with deionizer means actuation signals, said filter, temperature sensor, flow meter, and deionizer means being interconnected in a fluid series circuit, calibration means for selectively conditioning the corresponding deionized fluid sample stream in accordance with calibration actuation signals, to provide a conditioned deionized stream having predetermined chemical characteristics for calibration of downstream components, a first flow-splitter for dividing said extracted fluid sample stream into first and second fluid sample streams, and means for monitoring the specific conductivity of said first fluid sample stream, for monitoring chemical characteristics of said first fluid sample stream selected form the group of pH, dissolved oxygen, sodium, hydrazine, and ammonia, and for generating continuous monitor signal representative of the specific conductivity and the chemical characteristics so monitored;

a second flow-splitter for each of said second fluid sample streams for dividing the latter into respective third and fourth fluid sample streams;

means for monitoring the cation conductivity levels of each said third fluid sample streams and generating corresponding cation conductivity signals varying in accordance with the cation conductivity levels so monitored;

ion chromatograph means comprising:

anion chromatograph means for performing anion chromatography to monitor anions in one of the third fluid sample streams, and generating anion chromatograph signals representative of the anions so monitored, said anion chromatograph means having a sample volume control means for preparing a sample volume of one of the third fluid sample streams for monitoring in accordance with anion chromatograph sample volume control means actuation signals, and a detector, organic acid chromatograph means for performing organic acid chromatography to monitor organic acids in one of the third fluid sample streams, and generating organic acid chromatograph signals representative of the organic acids so monitored, said organic acid chromatograph means having a sample volume control means for preparing a sample volume of one of the third fluid sample streams for monitoring in accordance with organic acid chromatograph sample volume control means actuation signals, and a detector, cation chromatograph means for performing cation chromatography to monitor cations in one of the fourth fluid sample streams, and generating cation chromatograph signals representative of the cations so monitored, said cation chromatograph means having a sample volume control means for preparing a sample volume of one of the fourth fluid sample streams for monitoring in accordance with cation chromatograph sample volume control means actuation signals, and a detector, chromatograph selector means operable to alternatively direct one of the third fluid sample streams to either said organic acid chromatograph means or said anion chromatograph means in accordance with a chromatograph selector means actuation signal, an anion chromatograph eluant supply means for supplying an eluant to said anion chromatograph at a predetermine volumetric rate in accordance with anion chromatograph eluant supply means actuation signals, an organic acid chromatograph eluant supply means for supplying a selected one of plural eluants to said organic acid chromatograph at a predetermined volumetric rate in accordance with organic acid chromatograph eluant supply means actuation signals, and a cation chromatograph eluant supply means for supplying an eluant to said cation chromatograph at a predetermined volumetric rate in accordance with cation chromatograph eluant supply means actuation signals;

valve means operable to selectively direct said third fluid sample streams to said ion chromatograph means in accordance with a sampling sequence and to provide said fourth fluid sample streams to said ion chromatograph means in accordance with the sampling sequence; and control means for:

receiving said temperature, continuous monitor, cation conductivity, and anion, organic acid and cation chromatograph signals, determining said sampling sequence, comparing the cation conductivity of each third fluid sample stream with a cation conductivity alarm value an interrupting said sampling sequence if any of said cation conductivities exceeds said cation conductivity alarm value to provide the corresponding third and fourth fluid sample streams to said ion chromatograph means, calculating the sample volume of the third fluid sample stream to be prepared for monitoring by said anion and organic acid chromatograph sample volume control means in accordance with the monitored cation conductivity of the third fluid sample stream being supplied to said ion chromatograph means and stored data relating cation conductivity to ion concentration in a fluid sample, and generating said anion and organic acid chromatograph sample volume control means actuation signals and said anion and organic acid chromatograph eluant supply means actuation signals in accordance with the sample volume thus calculated, calculating the sample volume of the fourth fluid stream to be prepared for monitoring by said cation chromatograph sample volume control means in accordance with the specific conductivity of the fourth fluid sample stream being supplied to the ion chromatograph means and stored data relating specific conductivity to ion concentration in a fluid sample, and generating cation chromatograph sample volume control means actuation signals and said cation chromatograph eluant supply means actuation signals in accordance with the sample volume thus calculated, calculating a strong acid temperature compensated cation conductivity in accordance with the temperature conditions of the fluid sample stream being supplied to said ion chromatograph means, predetermined conductivity equations, and the anions and cations monitored by said anion and cation chromatographs, comparing said strong acid temperture compensated cation conductivity with the cation conductivity monitored by said means for monitoring cation conductivity levels to determine if organic acid chromatography is required, and selectively generating said chromatograph selector means actuation signals, calculating a cation conductivity including organic acids at the temperature conditions of the fluid sample stream being supplied to said ion chromatograph means in accordance with the anions, organic acids, and cations monitored by said anion, cation, and organic acid chromatographs and stored data, comparing temperature compensated cation conductivity including organic acids with the cation conductivity monitored by said means for monitoring cation conductivity levels to determine if calibration is required, and selectively generating said calibration actuation signals, and calibrating the continuous monitor, cation conductivity, and anion, organic acid and cation chromatograph signals using the conditioned dionized stream as a standard.

10. Apparatus as set forth in claim 9, wherein:

said plural eluants selectively supplied by said organic acid chromatograph eluant supply means include a pH3 and a pH4 eluant; and said control means determines if the time required for separation of fluoride ($F^-$) and formate in said organic acid chromatograph means is greater than one minute, generates said organic acid eluant supply means actuation signals so that said organic acid chromatograph eluant supply means supplies said pH4 eluant if the separation time is greater than one minute, and generates said organic acid chromatograph eluant supply actuation signals so that said eluant supply means supplies said pH3 eluant if the separation time is less than or equal to one minute.

11. Apparatus as set forth in claim 9, wherein:

said control means comprises:

a microcomputer, a bus, operatively connected to said microcomputer, a display, operatively connected to said bus, a printer, operatively connected to said bus, a chromatograph interface, operatively connected to said bus, and said anion, organic acid, and cation chromatograph means, a serial multiplexer, operatively connected to said bus, and a plurality of continuous monitor module means interfaces corresponding to respective ones of said continuous monitor module means, operatively connected to said serial multiplexer and respective ones of said continuous monitor module means;

said microcomputer generates deionizer unit control signals, calibration control signals, anion, organic acid and cation chromatograph eluant supply means control signals, anion, organic acid and cation chromatograph sample volume control means control signals, and chromatograph selector means control signals;

said chromatograph interface receives said anion, organic acid and cation chromatograph eluant supply means control signals, said anion, organic acid and cation chromatograph sample volume control means control signals, and said chromatograph selector means control signals, and generates, in accordance with said received control signals, said anion, organic acid and cation chromatograph eluant supply means acuatation signals, said anion, organic acid and cation chromatographs sample volume control means actuation signals, and said chromatograph selector means control signals; and each said continuous monitor module means interface receives said deionizer unit control signals and said calibration control signals and generates said deionizer unit control signals and said calibration actuation signals in accordance with said calibration control signals.

12. Apparatus for automatic, continuous on-line monitoring of the chemical characteristics of power plant steam cycle water at any one of a plurality of different points in the power plant steam cycle system, said water in the system at each point having characteristic temperature conditions and cation conductivity levels in addition to said chemical characteristics, said apparatus comrpising:

means for extracting, from at least a selected one of the plurality of points in the power plant steam cycle system, a corresponding, selected fluid sample stream;

a respectively associataed continuous monitor module for each selected fluid sample stream comprising means for monitoring the temperature conditions of the selected fluid sample stream and generating a corresponding temperature signal, calibration means operable for selectively conditioning the selected fluid sample stream in accordance with calaibration actuation signals to provide a conditioned calibration stream having predetermined chemical characteristics, and means for continuously monitoring at least one selected chemical characteristic of the selected fluid sample stream and, in response thereto, generating a corresponding continuous monitor signal;

means for receiving a poretion of each selected fluid sample stream and monitoring the cation conductivity levels thereof, and, in response thereto, generating a corresponding cation conductivity signal and providing a corresponding altered fluid stream from which cations have been removed;

ion chromatograph means for monitoring at least one chemical characteristic of each selected fluid sample stream and at least one selected chemical characteristic of the corresponding altered fluid stream in accordance with a chromatograph actuation signal, and, in response thereto, generating corresponding first and second chromatograph signals; and control means, responsive to at least the temperature signal, said corresponding cation conductivity signal and the first and second chromatogrph signals corresponding to each selected fluid sample stream, for calculating a derived cation conductivity for the respective, selected fluid sample stream in accordance with predetermined conductivity equations, comparing the derived cation conductivity with the cation conductivity monitored by said means for receiving for the respective fluid sample stream, and generating said calibration actuation signals and said chromatograph actuation signal in accordance with said comparison, for supply to said respectively associated continuous monitor module and said ion chromatograph means for the selected fluid sample stream.

13. Apparatus as set forth in claim 12, wherein:

said means for extracting is arranged to selectively extract a selected fluid sample stream from each of a plurality of points in the power plant steam cycle; and there is further provided:

a said continuous monitor module respectively associated with each of said selected fluid sample streams;

a said means for receiving respectively associated with each of said selected fluid sample streams; and means for selectively supplying said selected fluid sample streams and corresponding, altered fluid streams to said ion chromatograph means in individual succession, in accordance with a predetermined sampling sequence.

14. Apparatus as set forth in claim 13, wherein:

said steam cycle water and said altered fluid stream contain cations, organic acids and anions, and said ion chromatograph means comprises cation chromatograph means for monitoring cations in the selected fluid sample stream selectively supplied to said ion chromatograph, anion chromatograph means for monitoring anions in the corresponding, altered fluid stream, organic acid chromatograph means for monitoring organic acids in the corresponding, altered fluid stream, and means for providing the corresponding, altered fluid stream alternatively to either said anion chromatograph means or said organic acid chromatograph means in accordance with said chromatograph actuation signal;

said first chromatograph signal is generated in response to the cations so monitored, and said second chromatograph signal comprises an anion chromatograph signal generated in response to the anions so monitored and an organic acid chromatograph signal generated in response to the organic acids so monitored;

said derived cation conductivity includes a strong acid temperature compensated cation conductivity calculated in accordance with the monitored anions and cations;

said control means compares said strong acid temperature compensated cation conductivity with the cation conductivity monitored by said means for receiving to determine if organic acid chromatography is required and selectively generate said chromatograph actuation signal;

said derived cation conductivity includes a cation conductivity including organic acids at the monitored temperature calculated in accordance with the anions, organic acids and cations monitored by the ion chromatograph means; and said control means compares said calculated cation conductivity including organic acids at the monitored temperature conditions with the monitored cation conductivity levels to determine if calibration is required and selectively generates said calibration actuation signals.

15. Apparatus as set forth in claim 14, wherein:
- each continuously monitoring means comprises a specific conductivity monitor for monitoring the specific conductivity of a portion of the corresponding fluid sample stream, and, in response thereto, generating corresponding specific conductivity signals;
- said cation chromatograph means comprises sample volume control means responsive to a cation chromatograph sample volume control means actuation signal;
- said control means calculates a sample volume of the selected fluid sample stream selectively supplied to said ion chromatograph to be prepared for monitoring by said cation chromatograph sample volume control means in accordance with the monitored specific conductivity of the corresponding selected fluid sample stream and a predetermined equation relating specific conductivity to ion concentration in a fluid sample and generates the cation chromatograph sample volume control means actuator signal in accordance with the calculated sample volume;
- said anion and organic acid chromatograph means each comprises sample volume control means responsive to corresponding anion and organic acid chromatograph sample volume control means actuator signals; and
- said control means calculates a sample volume of the corresponding, altered fluid stream selectively supplied to said ion chromatograph and selectively provided to one of said anion and organic acid chromatograph means to be prepared for monitoring by said anion and organic acid chromatograph sample volume control means in accordance with the monitored cation conductivity of the corresponding altered fluid stream and a predetermined equation relating cation conductivity to ion concentration in a fluid sample and generates said anion and organic acid chromatograph sample volume control means actuator signals in accordance with the calculated sample volume.

16. Apparatus as set forth in claim 13, wherein each means for continuously monitoring comprises monitors for monitoring chemical characteristics of a portion of the fluid sample stream, the chemical characteristics being selected from the group of sodium, dissolved oxygen, hydrazine, ammonia, pH, and specific conductivity, and, in response thereto, generating coresponding continyous monitor signals.

17. Apparatus as set forth in claim 13, wherein said control means compares the monitored cation conductivity of each altered fluid sample stream with a cation conductivity alarm value and interrupts said predetermined sampling sequence if any of said monitored cation conductivities exceeds said cation conductivity alarm value to supply the altered fluid sample stream having a monitored cation conductivity exceeding said cation conductivity alarm value and the corresponding influent fluid sample stream to said ion chromatograph means.

* * * * *